US012690992B2

(12) United States Patent
Tokimoto et al.

(10) Patent No.: US 12,690,992 B2
(45) Date of Patent: Jul. 28, 2026

(54) COVER STENT

(71) Applicant: OLYMPUS CORPORATION, Tokyo (JP)

(72) Inventors: Takahira Tokimoto, Hachioji (JP); Toshiaki Hayashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 978 days.

(21) Appl. No.: 17/869,973

(22) Filed: Jul. 21, 2022

(65) Prior Publication Data

US 2022/0354674 A1    Nov. 10, 2022

Related U.S. Application Data

(63) Continuation of application No. PCT/JP2020/002809, filed on Jan. 27, 2020.

(51) Int. Cl.
A61F 2/90        (2013.01)

(52) U.S. Cl.
CPC ..................................... A61F 2/90 (2013.01)

(58) Field of Classification Search
CPC ...... A61F 2/86; A61F 2/90; A61F 2/07; A61F 2210/0076
See application file for complete search history.

(56) References Cited

U.S. PATENT DOCUMENTS 5,800,519 A * 9/1998 Sandock ................... A61F 2/90
                                                                 623/1.22
5,824,037 A    10/1998 Fogarty et al.

6,331,188 B1 * 12/2001 Lau ......................... A61F 2/915
                                                                 606/198
8,491,647 B2 * 7/2013 Colgan ..................... A61F 2/95
                                                                 606/198
8,814,927 B2 * 8/2014 Shin ......................... A61F 2/90
                                                                 623/1.15

(Continued)

FOREIGN PATENT DOCUMENTS

JP        2006297128 A    11/2006
JP        2010029685 A     2/2010

(Continued)

OTHER PUBLICATIONS

International Search Report dated Mar. 24, 2020 issued in PCT/JP2020/002809.

*Primary Examiner* — Tan-Uyen T Ho
(74) *Attorney, Agent, or Firm* — Scully, Scott, Murphy & Presser, P.C.

(57)        ABSTRACT

A cover stent includes: a mesh tube knitted into a tube by a wire including a first bending portion protruding toward a first end portion in a longitudinal direction of the tube and a second bending portion protruding toward a second end portion opposite to the first end portion in the longitudinal direction, the first and second bending portions intersecting each other by being twisted once; a cover covering outside or inside of the mesh tube; and a restricting member connected to the cover with a space, the wire in at least one of the first and second bending portions being movably inserted into the space along a surface of the cover. The mesh tube is connected to the cover by the restricting member so that the first and second bending portions can move relative to each other along the surface in the longitudinal direction.

1 Claim, 16 Drawing Sheets

(56)            References Cited

U.S. PATENT DOCUMENTS

| | | | |
|---|---|---|---|
| 8,968,384 B2 * | 3/2015 | Pearson | A61F 2/954 |
| | | | 623/1.13 |
| 9,504,555 B2 * | 11/2016 | Hartley | A61F 2/07 |
| 11,406,518 B2 * | 8/2022 | Mayberry | A61F 2/07 |
| 11,712,354 B2 * | 8/2023 | Wang | A61F 2/915 |
| | | | 623/1.15 |
| 2004/0111146 A1 | 6/2004 | McCullagh et al. | |
| 2007/0213805 A1 * | 9/2007 | Schaeffer | A61F 2/07 |
| | | | 623/1.13 |
| 2010/0318181 A1 * | 12/2010 | Shaolian | A61F 2/90 |
| | | | 623/1.35 |
| 2017/0119556 A1 * | 5/2017 | Holly | A61F 2/90 |
| 2017/0143467 A1 * | 5/2017 | Myung | A61L 31/10 |
| 2017/0189210 A1 * | 7/2017 | Kim | A61F 2/88 |
| 2022/0211524 A1 * | 7/2022 | Ide | A61F 2/852 |
| 2022/0257393 A1 * | 8/2022 | Ozawa | A61F 2/90 |
| 2022/0273473 A1 * | 9/2022 | Takita | A61F 2/90 |

FOREIGN PATENT DOCUMENTS

| | | | |
|---|---|---|---|
| JP | 2018505002 A | 2/2018 | |
| JP | 6350924 B2 | 7/2018 | |
| WO | 2016134148 A1 | 8/2016 | |
| WO | 2019078218 A1 | 4/2019 | |

* cited by examiner

COVER STENT

CROSS-REFERENCE TO RELATED APPLICATIONS

This application is a continuation application based on PCT Patent Application No. PCT/JP2020/002809, filed on Jan. 27, 2020, the entire content of which is hereby incorporated by reference.

BACKGROUND

Technical Field

The present invention relates to a cover stent.

Background Art

Various stents are known to maintain the shape of the lumen in a patient's body.

For example, Japanese Patent No. 6350924 (hereinafter referred to as Patent Document 1) describes a covered stent having a stent in which a wire is fence-knitted, an outer cover tape that covers the entire outer surface of the stent, and an inner cover tape that covers a part of the inner region of the stent.

According to the technique described in Patent Document 1, the stent is fixed to the outer cover tape that covers the entire outer surface of the stent by the inner cover tape that covers a part of the inner region of the stent. Since the covered stent described in Patent Document 1 has an outer cover tape, it is possible to prevent the biological tissue in the indwelling portion from biting into the stitch opening of the stent.

Furthermore, the cover stent can maintain the tubular shape due to the rigidity of the stent.

The stent can move along the surface of the outer cover tape at a site other than the fixed part of the inner cover tape. Therefore, the covered stent can be curved to some extent as a whole.

In the fixed part sandwiched and fixed by the inner cover tape and the outer cover tape, the cylindrical shape is maintained with almost no curvature. As a result, as shown in FIG. 15 in Patent Document 1, the shape at the time of bending is a polygonal line.

The covered stent described in Patent Document 1 may not be able to be curved by drawing a smooth curve along the lumen depending on the curved shape of the lumen. Therefore, the covered stent described in Patent Document 1 has a lower bending performance than a stent without a cover.

SUMMARY

The present invention provides a cover stent that can improve bending performance and shape maintenance performance.

A cover stent includes: a mesh tube knitted into a tube shape by a wire, the wire including a first bending portion protruding toward a first end portion in a longitudinal direction of the tube shape and a second bending portion protruding toward a second end portion opposite to the first end portion in the longitudinal direction, the first bending portion and the second bending portion intersecting each other by being twisted once; a cover that covers outside or inside of the mesh tube; and at least one restricting member connected to the cover with a space, the wire in at least one of the first bending portion and the second bending portion being movably inserted into the space along a surface of the cover, wherein the mesh tube is connected to the cover by the at least one restricting member so that the first bending portion and the second bending portion can move relative to each other along the surface at least in the longitudinal direction.

According to the cover stein of the above aspect, the bending performance and the shape maintenance performance can be improved.

BRIEF DESCRIPTION OF THE DRAWINGS

FIG. 9 is an operation explanatory view of a cover stent according to the first embodiment of the present invention.

FIG. 13 is a schematic diagram showing an example of a cover stent according to a second modification of the first embodiment of the present invention.

FIG. 14 is an operation explanatory diagram of a cover stent according to the second modification of the first embodiment of the present invention.

FIG. 15 is a schematic diagram showing an example of a cover stent according to a third modification of the first embodiment of the present invention.

FIG. 16 is a schematic diagram showing an example of a cover steal according to a fourth modification of the first embodiment of the present invention.

DETAILED DESCRIPTION OF THE PREFERRED EMBODIMENTS

Figure 1:
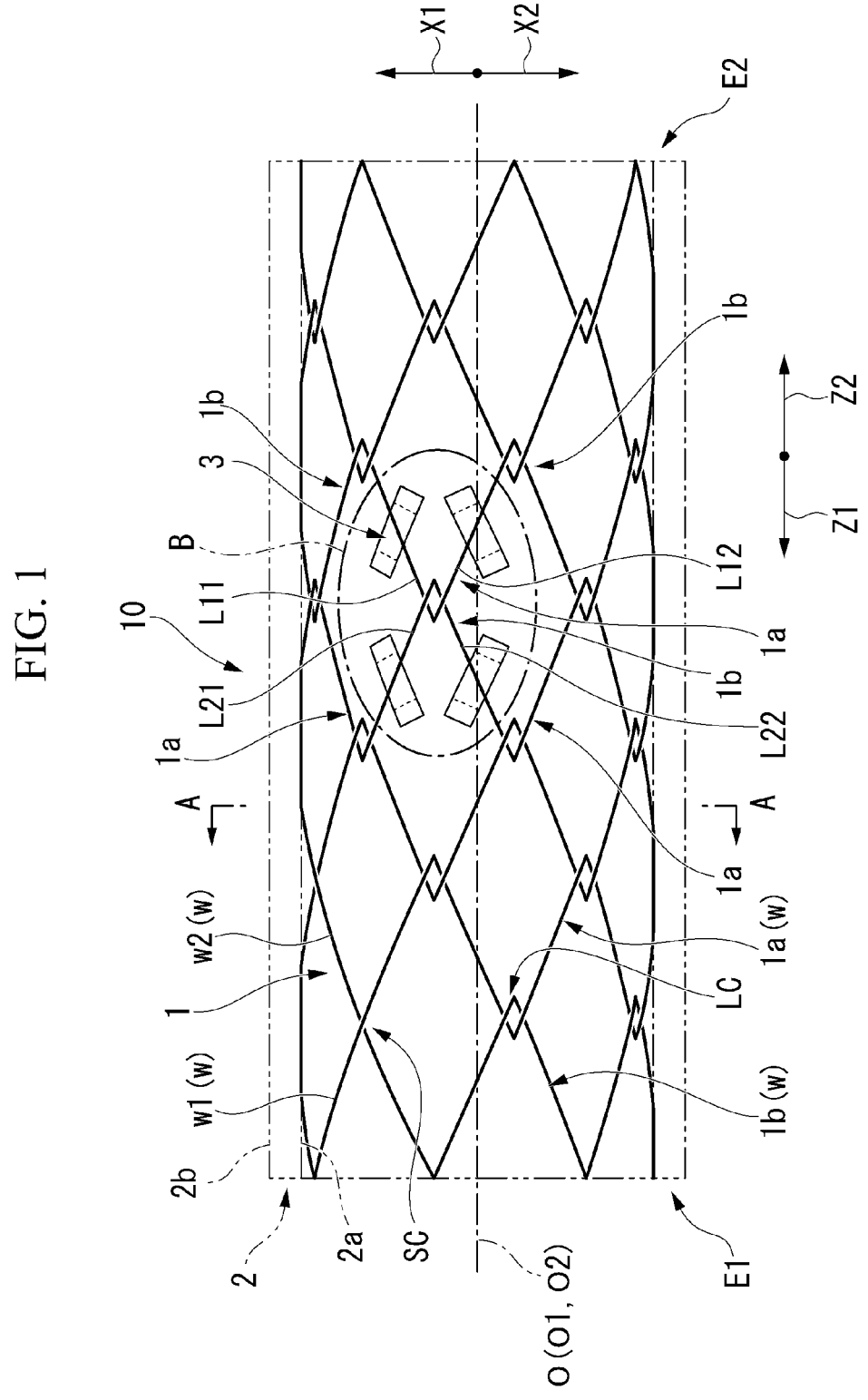
FIG. 1 is a schematic front view showing an example of a cover stent according to a first embodiment of the present invention.

Hereinafter, embodiments of the present invention will be described with reference to the accompanying drawings. In all the drawings, even if the embodiments are different, the same or corresponding members are designated by the same reference numerals, and common description will be omitted.

First Embodiment

The cover stent of the first embodiment of the present invention will be described.

Figure 2:
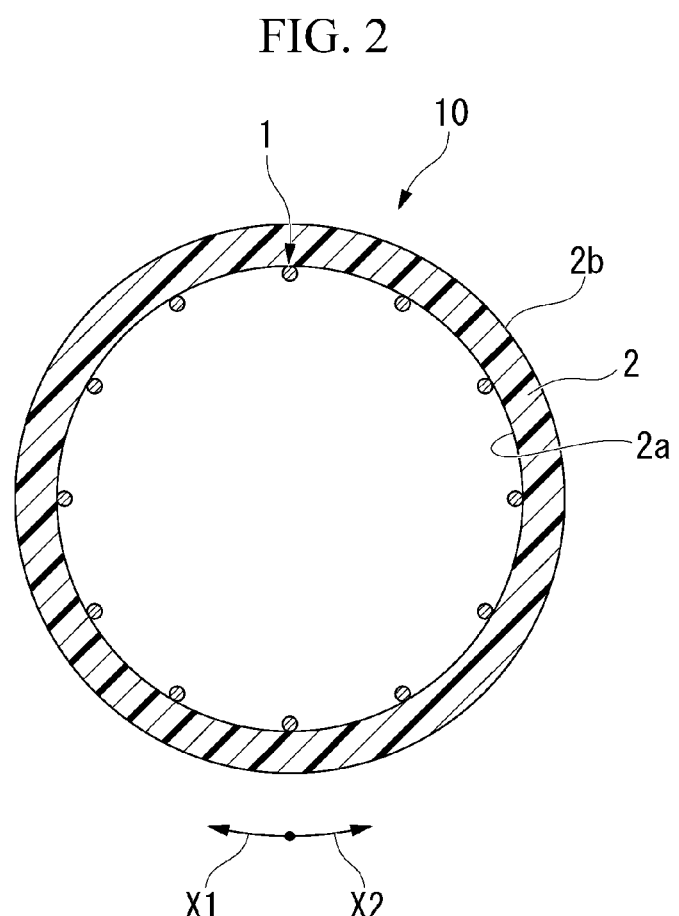
FIG. 2 is a cross-sectional view taken along the line A-A in FIG. 1.

FIG. 1 is a schematic front view showing an example of a cover stent according to the first embodiment of the present invention. FIG. 2 is a cross-sectional view taken along the line A-A in FIG. 1.

A cover stent 10 of the present embodiment shown in FIGS. 1 and 2 is formed in a circular tube shape (tube shape) as a whole. Hereinafter, the ends of the cover stem 10 in the longitudinal direction are referred to as a first end portion E1 (left side in FIG. 1) and a second end portion E2 (right side in FIG. 1). The direction from the second end E2 to the first end E1 along the longitudinal direction of the cover stent 10 is referred to as the Z1 direction, and the direction opposite to the Z1 direction in the longitudinal direction is referred to as the Z2 direction. When the direction in the Z1 direction and the Z2 direction is not specified, it may be simply referred to as the Z direction.

The cover stent 10 maintains a circular tube shape that extends straight due to the rigidity of a mesh tube 1 described later in the "undeformed state" that is not deformed by an external force. In the following, unless otherwise specified, the shape in the undeformed state will be described.

As shown in FIG. 1, the cover stent 10 includes the mesh tube 1, an outer cover 2 (cover), and a restricting member 3.

The mesh tube 1 and the outer cover 2 are substantially circular tubular members coaxial with each other. Therefore, in the following, when the relative positions of the cover stent 10 and its constituent members are described, the axial direction, the circumferential direction, and the radial direction may be used.

The axial direction is along the central axis O of the circular tube shape. Specifically, the axial direction is a direction along the central axis O2 of the outer cover 2 and the central axis O1 of the envelope surface of the outer periphery of the mesh tube 1. The axial directions of the outer cover 2 and the mesh tube 1 coincide with the respective longitudinal directions.

The circumferential direction is the direction that orbits around the central axis. The radial direction is a direction orthogonal to the central axis. The above directions are similarly defined with respect to the central axis of the curved tube even when the cover stent 10 is curved.

The mesh tube 1 is woven into a circular tube shape (see FIG. 2) with a wire w. The number of wires w may be one or more, but the mesh tube 1 will be described below with an example in which the mesh tube 1 is knitted with one wire w. Various knitting methods for forming a circular tube shape with one wire w are known.

The knitting method of the mesh tube 1 includes a first bending portion 1a and a second bending portion 1b formed by bending the wire w, and the first bending portion 1a and the second bending portion 1b are not particularly limited as long as they are twisted once and crossed with each other. The mesh tube 1 shown in FIG. 1 has an example of stitches.

Here, the expression "twisted once" is used to briefly explain an intersection path in which two wires w are twisted once and entangled with each other facing each other, and intersections are formed at two points. When viewed from the radial direction. As used herein, the embodiment is not limited to a mode in which the two yarns are twisted together in close contact with each other, for example, when the two yarns are twisted together.

The first bending portion 1a is a portion of the portion that is bent in a V shape when viewed from the radial direction of the cover stent 10 and protrudes toward the first end portion E1. Here, the V-shape includes a case of a V-shape having a pointed distal end and a case of a U-shape having a curved rounded distal end. For example, when the wire w is knitted using a manufacturing jig described later, a bending portion on an arc derived from the roundness of the pin in the manufacturing jig is formed in the bending portion. Since FIG. 1 is a schematic diagram, the first bending portion 1a is drawn in a V shape with a pointed distal end.

A plurality of first bending portions 1a are arranged adjacent to each other in the circumferential direction of the mesh tube 1 in the circumferential direction.

The second bending portion 1b is bent in a V shape when viewed from the radial direction of the cover stent 10, like the first bending portion 1a. The second bending portion 1b protrudes toward the second end portion E2.

Similar to the first bending portion 1a, a plurality of second bending portions 1b are arranged adjacent to each other in the circumferential direction of the mesh tube 1 in the circumferential direction.

In the mesh tube 1, most of the second bending portions 1b are formed at positions connecting two first bending portions 1a adjacent to each other in the circumferential direction.

The wire w in the mesh tube is bent in a zigzag shape, so that the first bending portion 1a and the second bending portion 1b are repeatedly formed and curved in a cylindrical shape around the central axis O2. The zigzag-shaped wires w are arranged axially offset at a pitch slightly shorter than the amplitude of the zigzag. When the unit of one pitch is referred to as a step, FIG. 1 shows, as an example, the mesh tube 11 in which a wire w is woven over seven steps.

The first bending portion 1a and the second bending portion 1b excluding both ends in the longitudinal direction (axial direction) of the mesh tube 1 intersect each other by being twisted once at positions facing each other in the axial direction of the mesh tube 1. A loop intersection LC is formed in this twisted portion. The detailed configuration in the vicinity of the loop intersection LC will be described later.

According to the above definition, the linear wire w is shared with the first bending portion 1a and the second bending portion 1b that are continuous with each other. In the present specification, in the description of the configuration around one loop intersection LC, the first bending portion 1*a* forming the loop intersection LC is assumed to be a V-shaped range up to each bent position of two consecutive second bending portions 1*b*. Similarly, the second bending portion 1*b* forming the loop intersection LC is assumed to be a V-shaped range up to each bent position of the two consecutive first bending portions 1*a*.

A straight line portion having a length approximately an integral multiple of the zigzag amplitude is formed at a portion where the zigzag-shaped wire w moves to adjacent stages in the axial direction. There are a plurality of such straight portions depending on the number of stages of the mesh tube 1. These plurality of straight portions intersect each other without being twisted. As a result, the mesh tube 1 is formed with an X-shaped simple intersection SC (intersection) when viewed from the radial direction.

When viewed from the radial direction, the mesh tube 1 is formed with a substantially rhombic opening having at least one of the loop intersection LC and the simple intersection SC at the apex. Hereinafter, this opening may be referred to as a stitch opening of the mesh tube 1.

As shown in FIGS. 1 and 2, the outer cover 2 is a circular tube having an inner peripheral surface 2*a* (the surface of the cover) on the inside and an outer peripheral surface 2*b* on the outside and covering the outside of the mesh tube 1. The diameter of the inner peripheral surface 2*a* is not particularly limited as long as the outer peripheral portion of the mesh tube 1 can be brought into contact with the entire outer peripheral portion. It is more preferable that the diameter of the inner peripheral surface 2*a* be substantially equal to the outer diameter of the mesh tube 1 in the undeformed state.

As the material of the outer cover 2, a material having biocompatibility and superior flexibility to the mesh tube 1 is selected. The thickness of the outer cover 2 is set so that the biological tissue that pushes the outer cover 2 from the outside does not sink into the inside of the mesh tube 1 through the stitch opening of the mesh tube 1 together with the outer cover 2.

The length of the outer cover 2 is not particularly limited as long as it does not interfere with the placement and removal of the cover stent 10. For example, the outer cover 2 may cover the entire length of the mesh tube 1, or may have a length such that at least one end of the mesh tube 1 in the axial direction protrudes outward in the axial direction.

For example, as the material of the outer cover 2, silicone, PTFE (polytetrafluoroethylene), or the like may be used.

Next, returning to the explanation of the mesh tube 1, the detailed configuration around the loop intersection LC will be explained.

Figure 3:
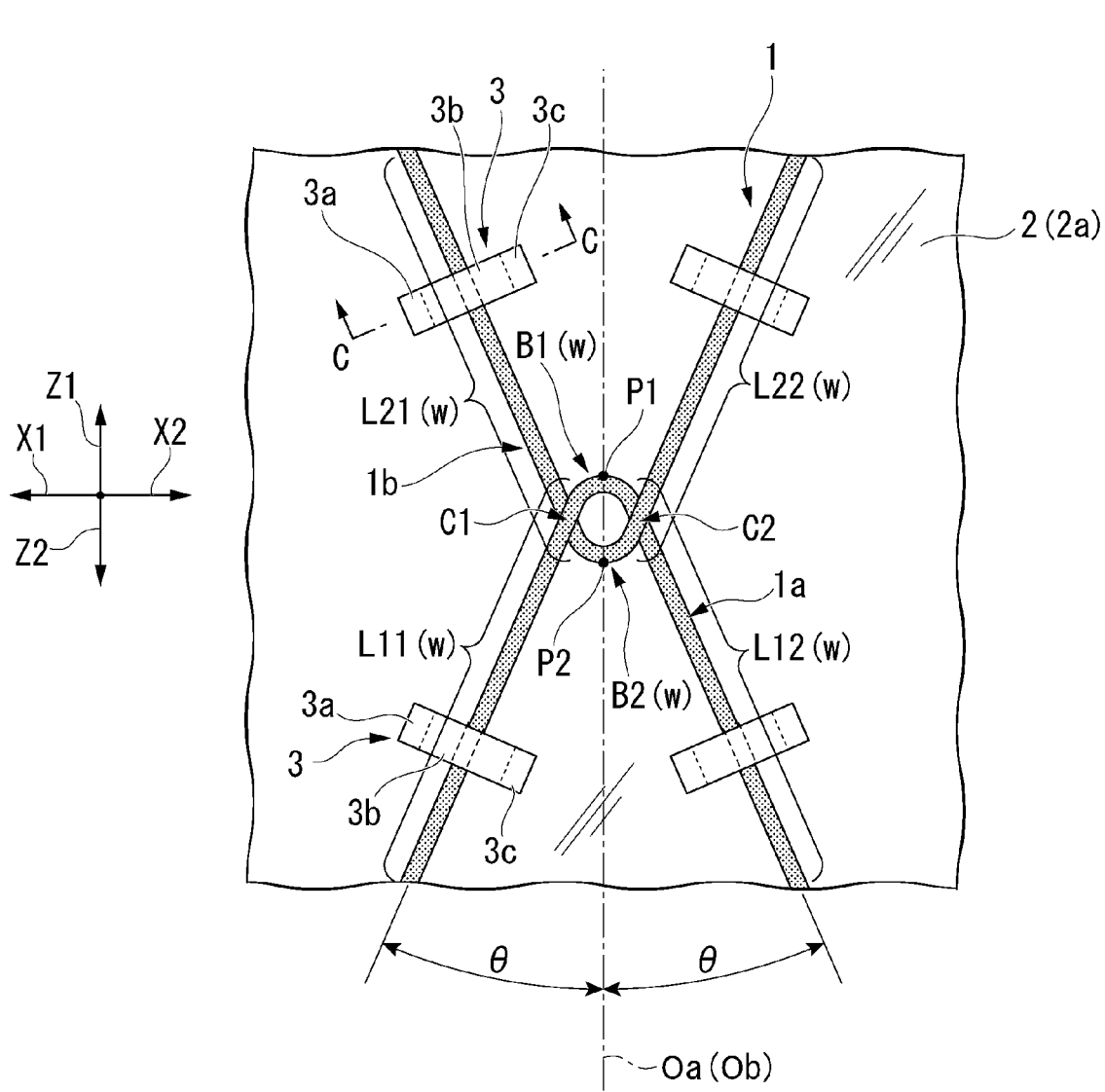
FIG. 3 is an enlarged view of part B in FIG. 1 viewed from the inside of the cover stent in a radial direction.

FIG. 3 is an enlarged view of the portion B in FIG. 1 viewed from the inside of the cover stent in the radial direction. In FIG. 3, the X1 direction means the clockwise direction when viewed in the Z1 direction among the circumferential directions of the cover stent 10. The X2 direction also means a counterclockwise direction. When the direction in the X1 direction and the X2 direction is not specified, it may be simply referred to as the X direction.

The first bending portion 1*a* has a V shape that narrows in the Z1 direction when viewed from the radial direction. The first bending portion 1*a* includes a bending portion B1, a first straight portion L11, and a second straight portion L12.

The bending portion B1 is an arcuate portion at the distal end portion in the protruding direction (Z1 direction) in the first bending portion 1*a*. A first apex P1 is formed at the distal end in the protruding direction.

The first straight line portion L11 and the second straight line portion L12 are straight lines that extend diagonally from both ends of the bending portion B1 in the X1 direction and the X2 direction as they proceed in the Z2 direction along the cylindrical surface, respectively. In the example shown in FIG. 3, the first straight line portion L11 extends from the end portion of the bending portion B1 in the X1 direction, and the second straight line portion L12 extends from the end portion of the bending portion B1 in the X2 direction. The first straight line portion L11 and the second straight line portion L12 extend with the first top portion P1 sandwiched between them while widening the distance between them.

The first straight line portion L11 and the second straight line portion L12 are inclined by θ with respect to the central axis Oa of the first bending portion 1*a* extending in the Z direction. Here, the angle is not particularly limited as long as it is an acute angle. It is more preferable that θ be larger than 0° and 45° or less.

The second bending portion 1*b* has a V shape that narrows in the Z2 direction when viewed from the radial direction. The second bending portion 1*b* includes a bending portion B2, a third straight portion L21, and a fourth straight portion L22.

The bending portion B2 is an arcuate portion at the distal end portion in the protruding direction (Z2 direction) in the second bending portion 1*b*. A second apex P2 is formed at the distal end in the protruding direction.

The third straight line portion L21 and the fourth straight line portion L22 are straight lines that extend diagonally from both ends of the bending portion B2 in the X1 direction and the X2 direction as they proceed in the Z2 direction along the cylindrical surface, respectively. In the example shown in FIG. 3, the third straight line portion L21 extends from the end portion of the bending portion B2 in the X1 direction, and the fourth straight line portion L22 extends from the end portion of the bending portion B2 in the X2 direction. The third straight line portion L21 and the fourth straight line portion L22 extend with the second top portion P2 sandwiched between them while widening the distance between them.

The third straight line portion L21 and the fourth straight line portion L22 are inclined by θ with respect to the central axis Ob of the second bending portion 1*b* extending along the Z direction, as in the case of the first bending portion 1*a*.

The first bending portion 1*a* and the second bending portion 1*b* are entwined so as to intersect each other at two points, the first intersection C1 and the second intersection C2, when viewed from the radial direction by twisting the wires w constituting each of them once.

In the example shown in FIG. 3, the wire w located in the X1 direction from the second top portion P2 in the second bending portion 1*b* is arranged along the inner peripheral surface 2*a* of the outer cover 2.

The wire w located in the X1 direction from the first top portion P1 in the first bending portion 1*a* rides on the second bending portion 1*b* from the inner peripheral surface 2*a*, and when viewed from the radial direction, it intersects with the second bending portion 1*b*.

Similarly, the wire w located in the X2 direction from the first top portion P1 in the first bending portion 1*a* is arranged along the inner peripheral surface 2*a*.

The wire w located in the X2 direction from the second top portion P2 in the second bending portion 1*b* rides on the first bending portion 1*a* from the inner peripheral surface 2*a*, and when viewed from the radial direction, it intersects with the first bending portion 1*a* at the second intersection C2.

Due to such entanglement of the wires w, a closed loop is formed when viewed from the radial direction by a part of the first bending portion 1a passing through the first intersection C1, the first top portion P1 and the second intersection C2, and a part of the second bending portion 1b passing through the second intersection C2, the second top portion P2 and the first intersection C1.

In the example shown in FIG. 3, the first intersection C1 is formed by the intersection of the first straight line portion L11 and the third straight the portion L21, and the second intersection C2 is formed by the intersection of the second straight line portion L12 and the fourth straight line portion L22. However, depending on the radius of curvature of the bending portions B1 and B2, the first intersection C1 and the second intersection C2 may be formed by the intersection of the bending portions B1 and B2.

An example of such a manufacturing method of the mesh tube 1 will be described.

Figure 4:
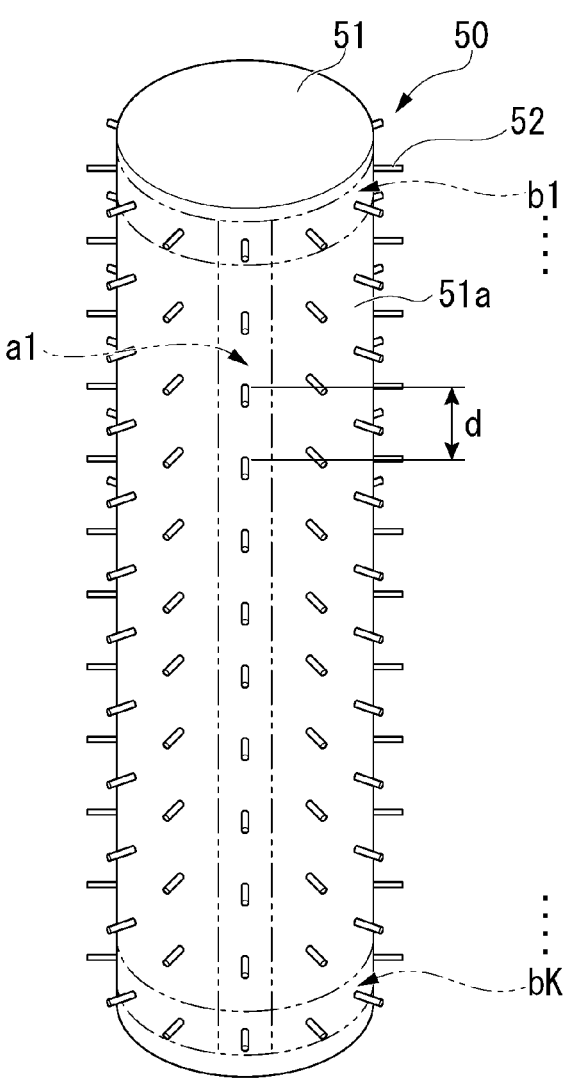
FIG. 4 is a schematic perspective view showing an example of a mesh tube manufacturing jig according to the first embodiment of the present invention.
Figure 5:
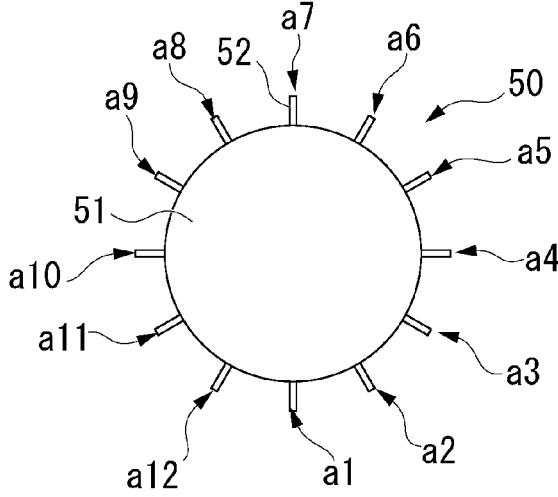
FIG. 5 is a schematic plan view showing an example of a mesh tube manufacturing jig according to the first embodiment of the present invention.
Figure 6:
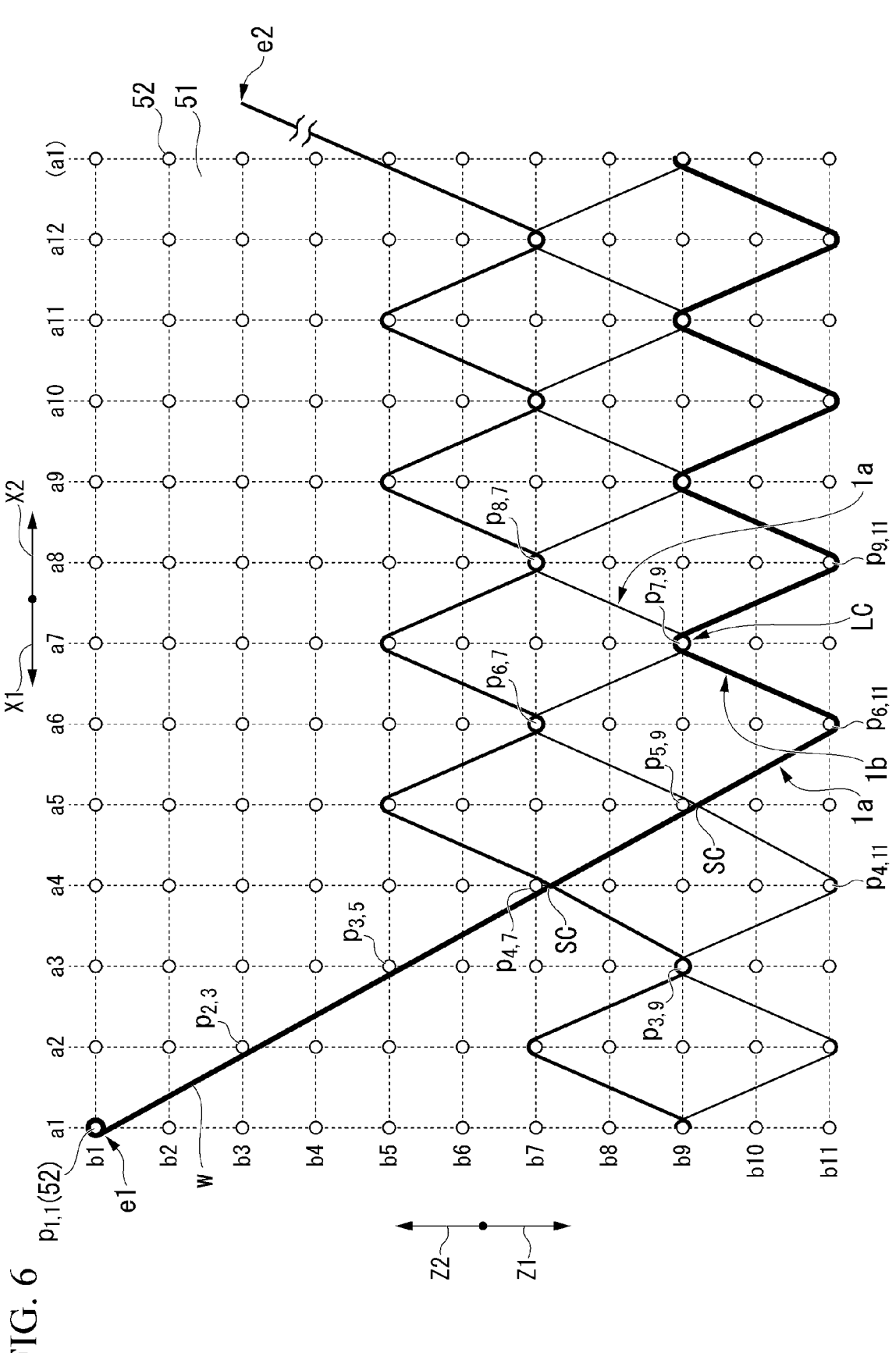
FIG. 6 is a schematic diagram showing an example of how to knit a mesh tube according to the first embodiment of the present invention.

FIG. 4 is a schematic perspective view showing an example of a mesh tube manufacturing jig according to the first embodiment of the present invention. FIG. 5 is a schematic plan view showing an example of a jig for manufacturing a mesh tube according to the first embodiment of the present invention. FIG. 6 is a schematic view showing an example of how to knit a mesh tube according to the first embodiment of the present invention.

The mesh tube 1 is manufactured for example, by using a jig 50 schematically shown in FIG. The jig 50 includes a substantially columnar core member 51 and a plurality of pins 52 for locking the wire w.

The diameter of an outer peripheral surface 51a of the core member 51 is substantially equal to the inner diameter of the mesh tube 1.

The plurality of pins 52 are provided on the core member 51 so as to protrude radially outward from the outer peripheral surface 51a. The plurality of pins 52 can be attached to and detached from the core member 51.

For example, the shape of each pin 52 is cylindrical. The outer diameter of each pin 52 is twice the radius of curvature inside the bending portions B1 and B2 described above.

Although not particularly shown, a groove passing near each pin 52 may be formed on the outer peripheral surface 51a for the purpose of facilitating braiding and crossing of the wire w.

Each pin 52 forms a row at equal intervals along the axial direction of the core member 51. Each pin 52 is arranged at a position that equally divides the circumference in the circumferential direction of the core member 51.

As shown in FIG. 5, the rows of the pins 52 are 12 rows from the row a1 to the row a12.

As shown in FIG. 4, twelve pins 52 arranged in the circumferential direction form a group arranged on a plane orthogonal to the axial direction of the core member 51. In the example shown in FIG. 4, the pin 52 constitutes the K group from the group b1 to the group bK. Here, K is an integer that is at least twice the number of stages of the mesh tube 1.

The arrangement pitch in the axial direction of each group is d. The size of the arrangement pitch of each group is about half the length of the step of the mesh tube 1.

The method of knitting the mesh tube 1 will be described with reference to FIG. 6. However, for the sake of simplification of illustration and description, the number of stages will be described as 5.

FIG. 6 is a developed view of the surface of the core member 51. At the right end of the drawing, the column a1 at the left end of the drawing is described. To knit the five-stage mesh tube 1, the pins 52 of the groups b1 to b11 are used. In the following, the pin 52 of the column a1 in the group bj is referred to as a pin $p_{i,j}$ (where i is an integer of 1 to 12 and j is an integer of 1 to 11).

The Z1 direction in the mesh tube 1 is the direction from the group b1 to the group b11.

As the material of the wire w forming the mesh tube 1, for example, a springy metal such as a superelastic alloy (NiTi alloy), SUS (stainless steel), or the like may be used.

For example, when the wire w is formed of a superelastic alloy containing NiTi as the main material, the wire w is not permanently deformed at the time of knitting as follows using the jig 50. The wire w is heat-treated in a braided state, so that the braided shape is retained.

The base end e1 of the wire w is fixed to the pin $p_{1,1}$. The wire w is pulled from the base end e1 along the sides of the pins $p_{2,3}$, $p_{3,5}$, $p_{4,7}$, $p_{5,9}$ in a substantially straight line. After that, the wire w is wound around the pin $p_{6,11}$ and then bent diagonally upward in the figure. Further, it is wound around the pin $p_{7,9}$ and then bent diagonally downward in the figure. As a result, a V-shaped bending portion convex in the Z1 direction is formed at the pin $p_{6,11}$.

After that, the wires w are wound around the pins 52 of the group b11 and the group b9 in a zigzag manner every other time in the circumferential direction.

As shown by a thin solid line, when the wire w is wound around the pin $p_{4,11}$, it is extended in a substantially straight line through the side of the pin $p_{5,9}$. The wire w passes on the thick solid wire w stretched between the pins $p_{1,1}$ and $p_{6,11}$. As a result, the first stage of the mesh tube 1 is formed.

A first bending portion 1a that does not form a loop intersection LC is formed on each pin 52 of the group b11. A simple intersection SC is formed in the vicinity of pin $p_{5,9}$.

The wire w is wound around the pin $p_{6,7}$ and then wound around the pins 52 of the group b9 and the group b7 in a zigzag manner. At this time, the wire w indicated by the thin solid wire is wound around each pin 52 while being twisted with the wire w indicated by the thick solid wire already wound around the group b9.

For example, the thin solid wire w wound around the pin $p_{7,9}$ passes between the thick solid wire w stretched between the pins $p_{7,9}$ and $p_{6,11}$ and the core member 51, and goes around the lower side of the pin $p_{7,9}$ in the figure. Further, the thin solid wire w passes over the thick solid wire w stretched between the pins $p_{7,9}$ and $p_{9,11}$ and is wound around the pin $p_{8,7}$.

In this way, around the pin $p_{7,9}$, the thick solid wire w forms the second bending portion 1b, and the thin solid wire w forms the first bending portion 1a. The first bending portion 1a and the second bending portion 1b form a loop intersection LC surrounding the pin $p_{7,9}$.

As shown by the thick solid line, when the wire w is wound around the pin $p_{3,9}$, it is extended in a substantially straight line through the side of the pin $p_{4,7}$. The wire w passes between the thick solid wire w stretched between the pins $p_{1,1}$ and $p_{6,11}$ and the core member 51. As a result, the second stage of the mesh tube 1 is formed.

A simple intersection SC is formed in the vicinity of the pin $p_{4,7}$.

By repeating the above in the same manner, the third, fourth, and fifth stages are sequentially formed. When the distal end e2 of the wire w reaches the $p_{1,1}$ it is joined to the proximal end e1.

After that, when an appropriate heat treatment is performed, the bending portion of the wire w is permanently deformed and the bent shape is memorized.

In this way, a five-stage mesh tube 1 is formed on the jig 50.

After that, the pin 52 is removed from the core member 51, and the mesh tube 1 is removed from the core member 51.

A plurality of simple intersections SC are formed by the intersection of the thick solid wire w stretched between the pins $p_{1,1}$ and $p_{6,11}$ and the wire w stretched on another path.

At the boundary of each stage except for the plurality of simple intersections SC, the first bending portion 1$a$ and the second bending portion 1$b$ are twisted once so that the stages are movably connected to each other in the axial direction. A loop intersection LC is formed at each of the twisted portions of the first bending portion 1$a$ and the second bending portion 1$b$.

As shown in FIG. 1, the restricting member 3 is a member connected by the outer cover 2 and the inner peripheral surface 2$a$, and through which a wire w forming at least one of the first bending portion 1$a$ and the second bending portion 1$b$ is inserted between the inner peripheral surface 2$a$ and the restricting member 3. The restricting member 3 restricts the moving range of the inserted wire w.

As shown in FIG. 3, each restricting member 3 covers the first straight line portion L11, the second straight line portion L12, the third straight line portion L21, and the fourth straight line portion L22 from the inside of the outer cover 2 in a direction orthogonal to each extending direction. The shape of the restricting member 3 when viewed from the radial direction is a strip shape long in the transverse direction of each straight line portion.

Since the configuration and arrangement form of each restricting member 3 are the same, the following will be described with an example of the restricting member 3 through which the third straight line portion L21 is inserted.

Figure 7:
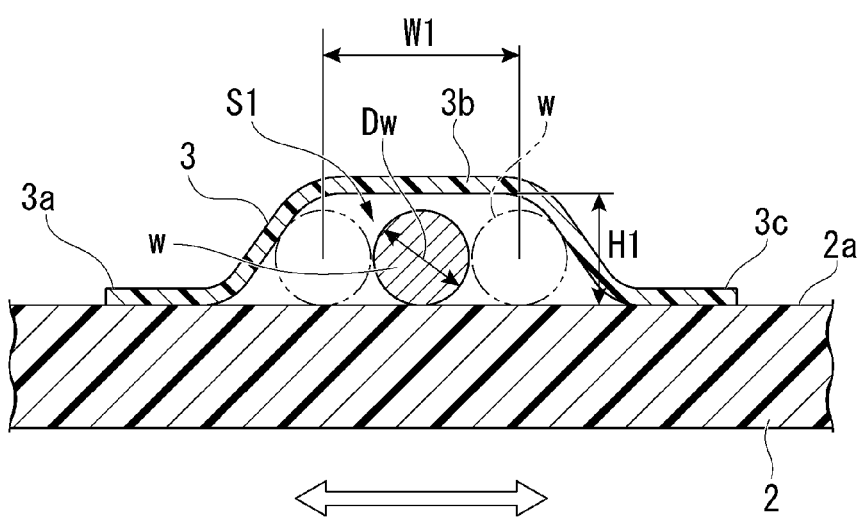
FIG. 7 is a cross-sectional view taken along the line C-C in FIG. 3.

FIG. 7 is a sectional view taken along the line C-C in FIG. 3.

As shown in FIG. 7, the restricting member 3 includes joint portions 3$a$ and 3$c$, and a position restricting portion 3$b$.

The joint portions 3$a$ and 3$c$ are provided at both ends of the restricting member 3 in the longitudinal direction, and are respectively joined to the outer cover 2. Examples of the joining method of the joint portions 3$a$ and 3$c$ with the outer cover 2 include fusing, bonding, thermocompression bonding, and heat welding.

In each restricting member 3, the joint portion 3$a$ is located closer to the X1 direction than the wire w inserted through the restricting member 3. The joint portion 3$c$ is located closer to the X2 direction than the wire w inserted through the restricting member 3.

The position restricting portion 3$b$ is a portion connecting the joint portions 3$a$ and 3$c$, and is formed apart from the inner peripheral surface 2$a$. In the example shown in FIG. 7, the position restricting portion 3$b$ is formed in a substantially trapezoidal shape in a cross section along the longitudinal direction thereof. That is, the position restricting portion 3$b$ extends diagonally inward from the end of the joint portion 3$a$, has a substantially constant height from the inner peripheral surface 2$a$ (flat portion), and extends diagonally outward in the radial direction and is connected to the end portion of the joint portion 3$c$.

Between the position restricting portion 3$b$ and the inner peripheral surface 2$a$, a space S1 is formed in which the wire w can be inserted and the inserted wire w can move at least along the longitudinal direction (axial direction) of the mesh tube 1.

In the space S1, it is more preferable that the size between the flat portion of the position restricting portion 3$b$ and the inner peripheral surface 2$a$ be H1 (first size), which is substantially equal to the diameter Dw of the wire w. That is, the wire w inserted through the restricting member 3 may be in contact with the restricting member 3 and the inner peripheral surface 2$a$ (H1=Dw), or may be separated from the restricting member 3 (H1>Dw).

In the space S1, the size of the restricting member 3 in the longitudinal direction is such that the wire w can move in the longitudinal direction between the joint portions 3$a$ and 3$c$. In the example shown in FIG. 7, the wire w in contact with the inner peripheral surface 2$a$ can move within the space S1 within the range of the length W1 (W1>Dw).

In this case, the wire w can move in the space S1 along the circumferential direction of the outer cover 2 (X direction in FIG. 3) in the range of W1×cos θ (second size). The second size is larger than the first size.

The size of W1 defines the size at which the first bending portion 1$a$ or the second bending portion 1$b$ inserted through the restricting member 3 can move in the axial direction of the outer cover 2. The size of W1 is appropriately set according to the amount of axial movement of the outer cover 2 required for the first bending portion 1$a$ or the second bending portion 1$b$ inserted through the restricting member 3.

The material of the restricting member 3 is not particularly limited as long as it can be joined to the outer cover 2 and the space S1 can be formed. The restricting member 3 is more preferably formed of a flexible material that can be deformed along the curved shape when the cover stent 10 is curved. For example, as the material of the restricting member 3, silicone, polyethylene. PTFE (polytetrafluoroethylene) or the like may be used.

In manufacturing the restricting member 3, the shapes of the joint portions 3$a$ and 3$b$ and the position restricting portion 3$b$ may be formed before joining with the outer cover 2, or the shapes of the joint portions 3$a$ and 3$b$ and the position restricting portion 3$b$ may be formed by deforming the flat strip-shaped member at the time of joining with the outer cover 2.

The cover stent 10 described above is manufactured by preparing a mesh tube 1 by knitting a wire w, inserting the mesh tube 1 into the inside of the outer cover 2, and then joining the restricting member 3 to the outer cover 2.

The action of the cover stent 10 will be explained focusing on the bending motion.

Figure 8:
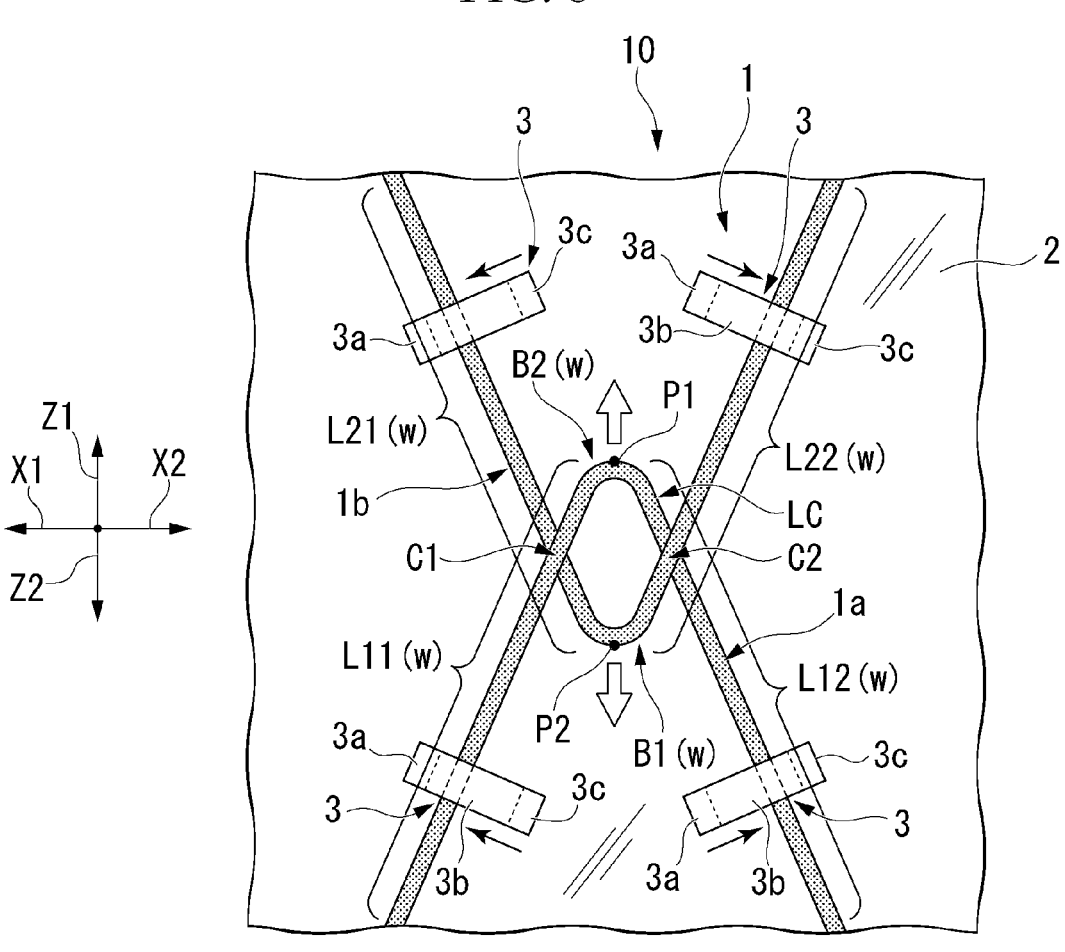
FIG. 8 is an operation explanatory view of a cover stent according to the first embodiment of the present invention.
Figure 9:
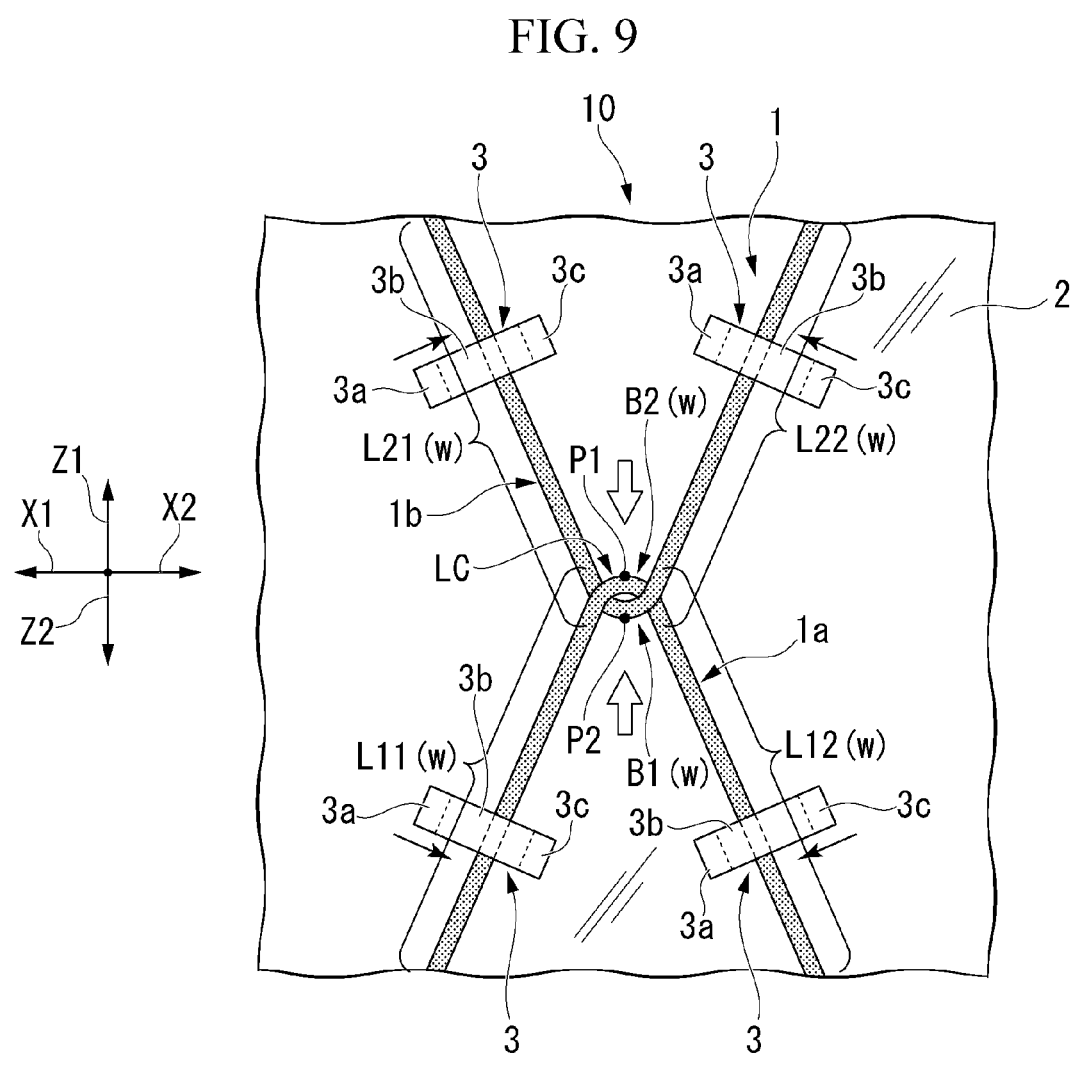
Figure 10:
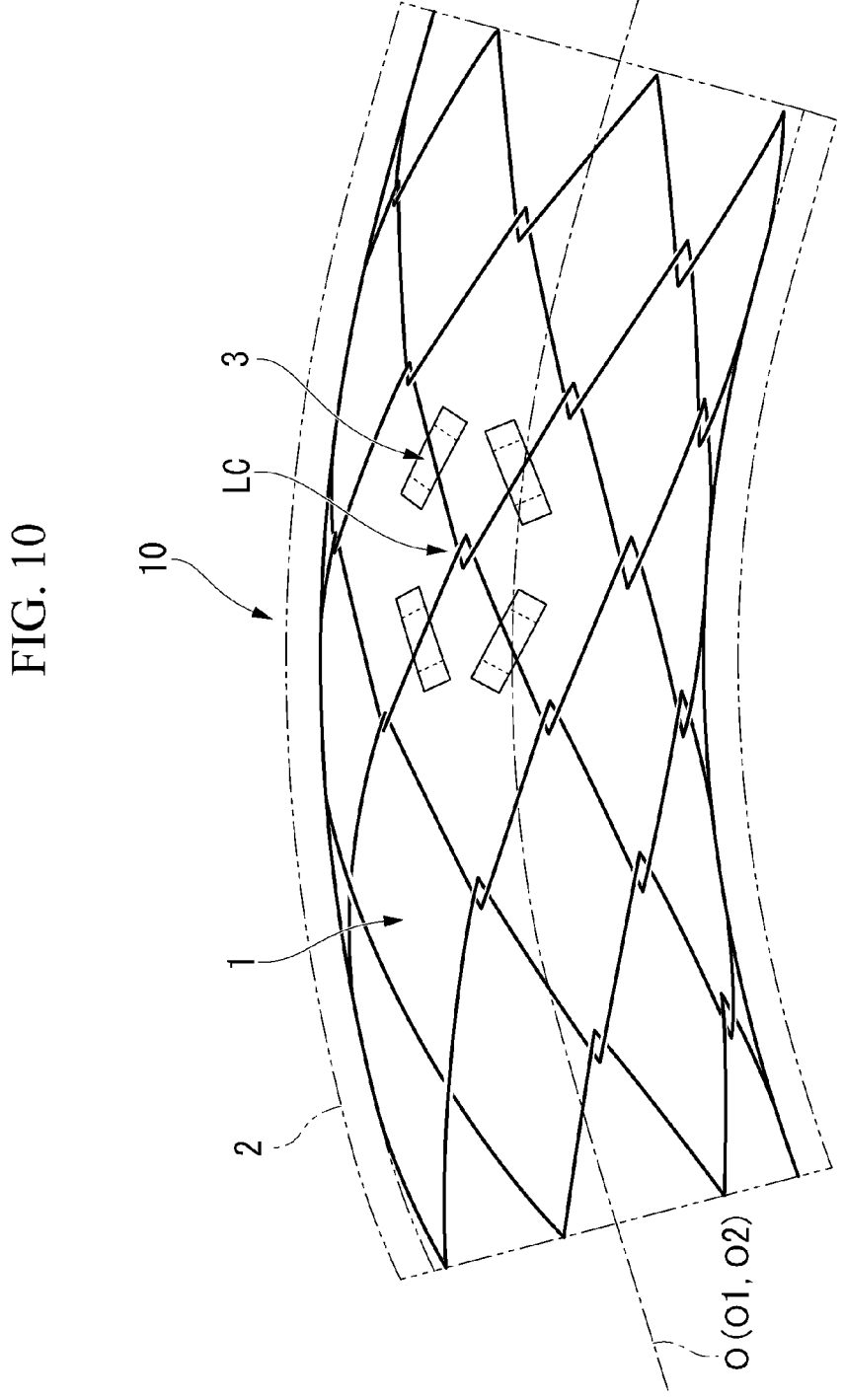
FIG. 10 is a schematic front view showing the curved shape of the cover stent according to the first embodiment of the present invention.

FIGS. 8 and 9 are operation explanatory views of the cover stent according to the first embodiment of the present invention. FIG. 10 is a schematic front view showing the curved shape of the cover stent according to the first embodiment of e present invention.

In the cover stent 10, the mesh tube 1 and the outer cover 2 are arranged coaxially with each other. The outer peripheral portion of the mesh tube 1 is in contact with the inner peripheral surface 2$a$ of the outer cover 2. The mesh tube 1 is connected to the outer cover 2 via a restricting member 3 joined to the outer cover 2.

The moving range of the wire w inserted through the restricting member 3 is restricted to the range passing through the space S1 of the restricting member 3. As a result, the movement range in the direction along the inner peripheral surface 2$a$ of the first bending portion 1$a$ or the second bending portion 1$b$ inserted through the restricting member 3 is also restricted by the restricting member 3.

For example, as shown in FIG. 8, the movable amount of the first bending portion 1$a$ in the Z1 direction is defined by the movable amount closer to the joint portion 3a in the restricting member 3 through which the first straight line portion L11 is inserted, and the movable amount closer to the joint portion 3c in the restricting member 3 through which the second straight portion L12 is inserted.

Similarly, the movable amount of the second bending portion 1b in the Z2 direction is defined by the movable amount of the second bending portion 1b in the Z2 direction is the movable amount closer to the joint portion 3a in the restricting member 3 through which the third straight line portion L21 is inserted, and the movable amount closer to the joint portion 3c in the restricting member 3 through which the fourth straight line portion L22 is inserted.

For example, when each wire w in the undeformed state can move W1/2 along the longitudinal direction of each restricting member 3, the movable amount of the first bending portion 1a in the Z1 direction is $W1/(2\times\sin\theta)$. Similarly, the movable amount of the second bending portion 1b in the Z2 direction is $W1/(2\times\sin\theta)$.

As described above, the first bending portion 1a and the second bending portion 1b constituting the loop intersection LC are relatively movable in the direction away from each other in the Z direction. When they move away from each other in the Z direction from the undeformed state, the positions of the first intersection C1 and the second intersection C2 change, and the range inside the loop intersection LC expands as compared with the undeformed state.

As shown in FIG. 9, the movement in the direction opposite to that of FIG. 8 is similarly restricted by each restricting member 3.

For example, when each wire w in the undeformed state can move W1/2 along the longitudinal direction of each restricting member 3, the movable amount of the first bending portion 1a in the Z2 direction is $W1/(2\times\sin\theta)$. Similarly, the movable amount of the second bending portion 1b in the Z1 direction is $W1/(2\times\sin\theta)$.

As described above, the first bending portion 1a and the second bending portion 1b constituting the loop intersection LC can move relative to each other in the Z direction. When they approach each other in the Z direction from the undeformed state, the positions of the first intersection C1 and the second intersection C2 change, and the range inside the loop intersection LC is reduced as compared with the undeformed state.

However, if the surface on the back side of the first top portion P1 in the bending portion B1 and the surface on the back side of the second top portion P2 in the bending portion B2 come into contact with each other, they cannot be further separated from each other.

As described above, since the mesh tube 1 is movably connected to the inner peripheral surface 2a of the outer cover 2 via the restricting member 3, the first bending portion 1a and the second bending portion 1b constituting the loop intersection LC can move relative to each other at least in the axial direction.

As a result, as shown in FIG. 10, when the cover stent 10 is bent, the first bending portion 1a and the second bending portion 1b move relative to each other, and the loop intersection LC expands as it approaches the inside of the bend on the lower side of the figure, and the loop intersection LC shrinks as it approaches the outside of the bend on the upper side of the figure. At this time, since the wire w is not directly joined to the outer cover 2, it easily moves relative to the outer cover 2.

As a result, the cover stent 10 is easily and smoothly curved, so that the curved shape of the cover stent 10 becomes a smooth curved surface.

In this curved state, the wire w in each stage of the mesh tube 1 urges the inner peripheral surface 2a of the outer cover 2 radially outward. As a result, even if an external force acts on the cover stent 10 from the outside in the radial direction, the circular shape of the lumen of the cover stent 10 is maintained by the rigidity of the mesh tube 1. As a result, even if the bending is easy, deformation of a kink or the like can be suppressed, and good shape maintenance performance can be obtained.

When the cover stent 10 is curved, the first bending portion 1a and the second bending portion 1b whose positions are restricted by the restricting member 3 do not move beyond the restricted range of the restricting member 3. As a result, the amount of curvature of the mesh tube 1 is limited to some extent. As a result, even if it is easy to bend, it is difficult for a large deformation to occur in which the shape before bending cannot be restored due to an excessive external force. From such a viewpoint, it is more preferable that the restricting member 3 be arranged substantially evenly with respect to each loop intersection LC in the cover stent 10.

For example, all of the first bending portion 1a and the second bending portion 1b forming the loop intersection LC may be connected to the outer cover 2 via the restricting member 3.

For example, in the axial direction or the circumferential direction, the first bending portion 1a, and the second bending portion 1b forming the loop intersection LCs located at intervals of a certain number may be connected to the outer cover 2 via the restricting member 3.

The cover stent 10 is used to maintain the shape of the lumen in the patient's body. The cover stent 10 is placed in the patient's lumen by an appropriate delivery system. At that time, the lumen is curved depending on the type and site of the lumen.

Since the cover stent 10 has excellent bending performance, it is possible to expand its inner diameter along the bending of the lumen at the time of indwelling.

Further, even when the cover stent 10 is removed from the lumen of the patient, the cover stent 10 can be easily curved along the curvature of the lumen of the removal route, so that the load on the patient at the time of removal can be reduced.

According to the cover stent 10, since the mesh tube 1 is covered with the outer cover 2, the external biological tissue does not bite into the inside of the mesh tube 1 from the stitches of the mesh tube 1. Therefore, restenosis can be suppressed.

As described above, according to the cover stent 10 of the present embodiment, the bending performance and the shape maintaining performance can be improved.

Next, the first to ninth modifications of the present embodiment will be described.

First Modification

Figure 11:
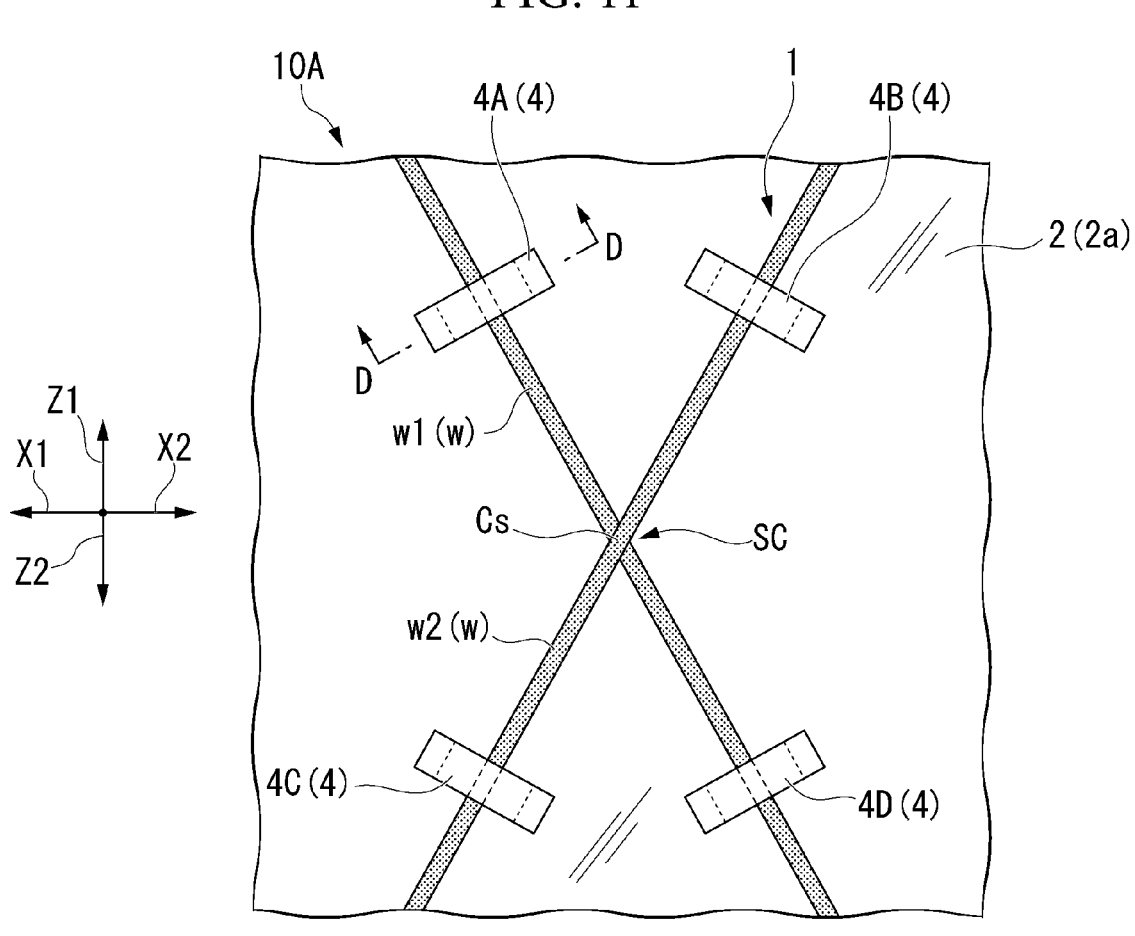
FIG. 11 is a schematic diagram showing an example of a cover stent according to a first modification of the first embodiment of the present invention.
Figure 12:
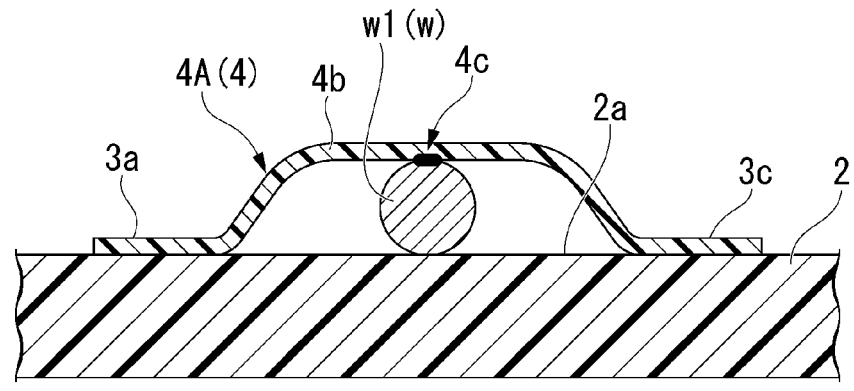
FIG. 12 is a cross-sectional view taken along the line D-D in FIG. 11.

FIG. 11 is a schematic diagram showing an example of a cover stent according to a first modification of the first embodiment of the present invention. FIG. 11 is a view seen in the radial direction from the inside of the cover stent (the same applies to FIGS. 13 to 18 and 20 described later). FIG. 12 is a cross-sectional view taken along the D-D FIG. 11.

As shown in FIG. 11, the cover stent 10A of the first modification further includes a joining member 4 in addition to the restricting member 3 in the first embodiment. The joining member 4 is provided at at least one simple intersection SC in the mesh tube 1 as needed. Hereinafter, the points different from the first embodiment will be mainly described.

The joining member 4 joins the wires w1 and w2 forming the simple intersection SC in the mesh tube 1 to the outer cover 2. When viewed from the radial direction, the wires w1 and w2 intersect each other in an X-shape at the intersection Cs.

The wires w1 and w2 are composed of straight portions included in the first bending portion 1*a* or the second bending portion 1*b* whose bending portion is not shown. In the example shown in FIG. 11, the wire w2 sandwiches the wire w1 with the inner peripheral surface 2*a* at the intersection Cs.

In the example shown in FIG. 11, the joining member 4 is composed of four joining members 4A, 4B, 4C, and 4D.

The joining members 4A and 4D each join the wire w1 to the outer cover 2 at two positions facing each other across the intersection Cs.

The joining members 4B and 4C each join the wire w2 to the outer cover 2 at two positions facing each other across the intersection Cs.

Since the configurations of the joining members 4 are similar to each other, an example of the joining member 4A will be described.

As shown in FIG. 12, the joining member 4A includes a wire pressing portion 4*b* instead of the position restricting portion 3*b* of the restricting member 3. The wire pressing portion 4*b* presses the wire w1 against the inner peripheral surface 2*a*. A wire bonding portion 4*c* to be bonded to the wire w1 is formed at the wire pressing portion 4*b*, the wire w1, and the abutting portion.

For example, the wire bonding portion 4*c* may be formed by fusion bonding, adhesion, or the like.

The joining member 4A may be formed by using the same member as the restricting member 3. In this case, a member similar to the restricting member 3 may be joined to the outer cover 2 at the joint portions 3*a* and 3*c*, and the wire joint portion 4*c* may be formed at the portion corresponding to the position restricting portion 3*b* at the time of joining or after joining.

According to this modification, the wires w1 and w2 forming the simple intersection SC are fixed to the outer cover 2 by the joining members 4A, 4B, 4C, and 4D provided at four points surrounding the intersection Cs.

Although the case where the number of the joining members 4 is 4 has been described above, the number of the joining members 4 is not limited to 4 as shown in the figure if at least one of the wires w1 and w2 forming the simple intersection SC is joined.

For example, at least one of the joining members 4A, 4B, 4C, and 4D may be provided as the joining member 4.

For example, the number of the joining members 4 is more preferably two or more for joining the wires w1 and w2, respectively.

For example, when fixing only one of the wires w1 and w2, it is more preferable to use at least one of the joining members 4B and 4C to join the wire w2 sandwiching the wire w1 with the outer cover 2 to the outer cover 2.

Second Modification

Figures 13, 14:
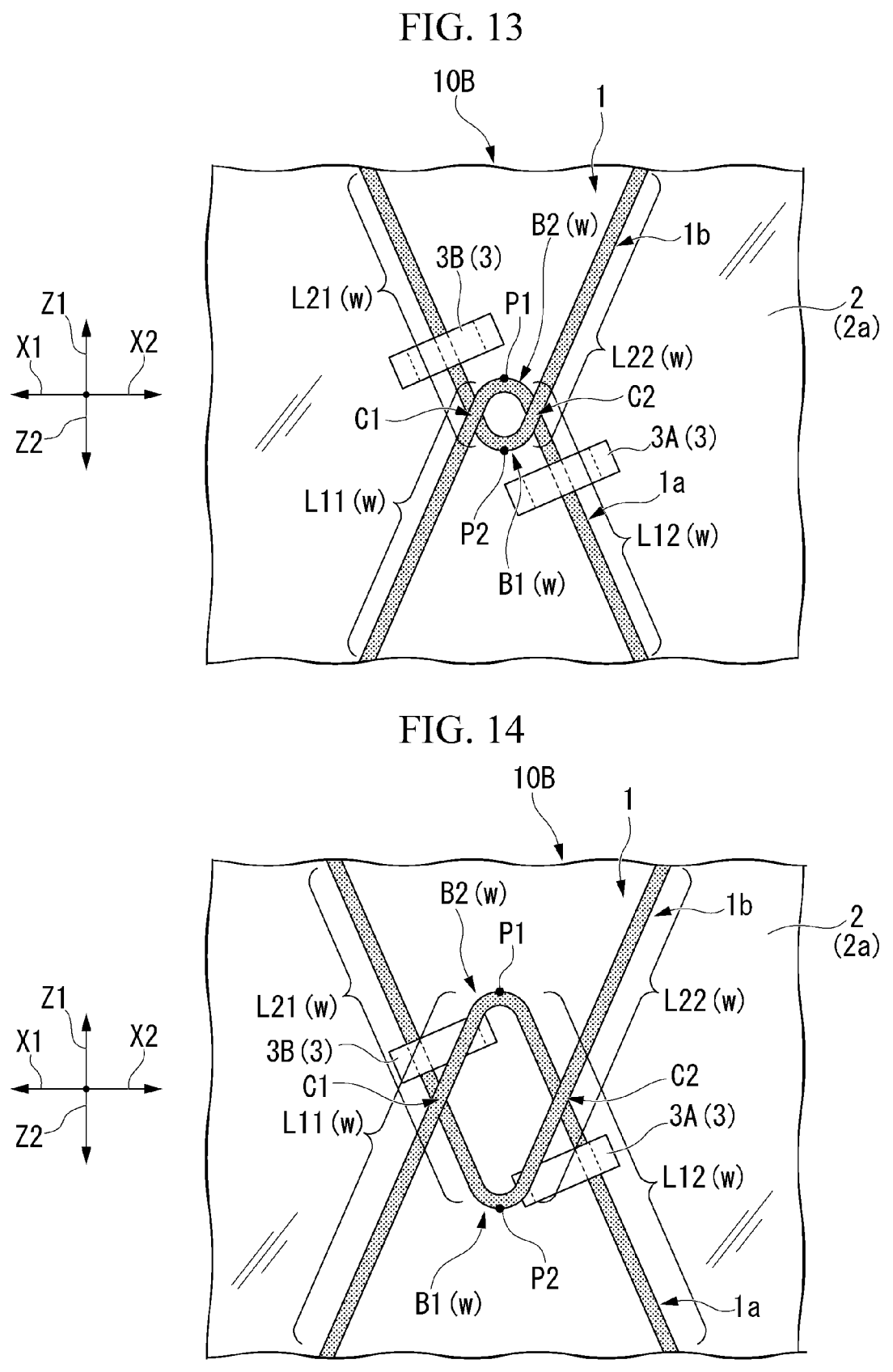

FIG. 13 is a schematic diagram showing an example of a cover stent according to a second modification of the first embodiment of the present invention. FIG. 14 is an operation explanatory diagram of the cover stent according to the second modification of the first embodiment of the present invention.

As shown in FIG. 13, the second modification is a particularly suitable example when two restricting members 3 are provided in the vicinity of the loop intersection LC.

The cover stent 10B of the present modification includes the restricting members 3A and 3B in place of the four restricting members 3 in the first embodiment. The configurations of the restricting members 3A and 3B are the same as those of the restricting member 3. Hereinafter, the points different from the first embodiment will be mainly described.

The restricting member 3A is a member through which the second straight line portion L12 of the first bending portion 1*a* is inserted. The second straight line portion L12 is located closer to the outer cover 2 than the fourth straight line portion L22 at the second intersection C2. That is, the second straight line portion L12 enters between the outer cover 2 and the fourth straight line portion L22 and intersects with the fourth straight line portion L22.

The restricting member 3B is a member through which the third straight line portion L21 of the second bending portion 1*b* is inserted. The third straight line portion L21 is located closer to the outer cover 2 than the first straight line portion L1 at the first intersection C1. That is, the third straight line portion L21 enters between the outer cover 2 and the first straight line portion L11 and intersects with the first straight line portion L11.

According to such a positional relationship, as shown in FIG. 14, when the first bending portion 1*a* moves in the Z1 direction, the first straight line portion LH is along the upper side (front side of the illustrated paper surface) of the third straight line portion L21. The first straight line portion L11 can move through the upper side of the restricting member 3B.

Similarly, when the second bending portion 1*b* moves in the Z2 direction, the fourth straight line portion L22 moves along the upper side (front side of the illustrated paper surface) of the second straight line portion L12, so that the fourth straight line portion L22 can move through the upper side of the restricting member 3A.

However, contrary to the above, in a case where the first straight line portion L11 and the fourth straight line portion L22 are inserted through the restricting member 3, when the first bending portion 1*a* moves in the Z1 direction, since the second straight line portion L12 moves between the fourth straight line portion L22 and the inner peripheral surface 2*a*, it cannot move in the Z1 direction beyond the restricting member 3 through which the fourth straight line portion L22 is inserted.

Similarly, when the second bending portion 1*b* moves in the Z2 direction, the first straight portion L11 cannot move in the Z2 direction beyond the restricting member 3 through which the first straight portion L11 is inserted.

Therefore, when the restricting member 3 is arranged near the loop intersection LC, the amount of movement of the first bending portion 1*a* and the second bending portion 1*b* in the axial direction is smaller than that of the present modification.

According to this modification, even if the restricting members 3A and 3B are arranged in the vicinity of the loop intersection LC in the undeformed state, since the limitation of the relative movement amount of the first bending portion 1a and the second bending portion 1b in the axial direction is reduced, the bending performance is further improved.

Third Modification Example

Figures 15, 16:
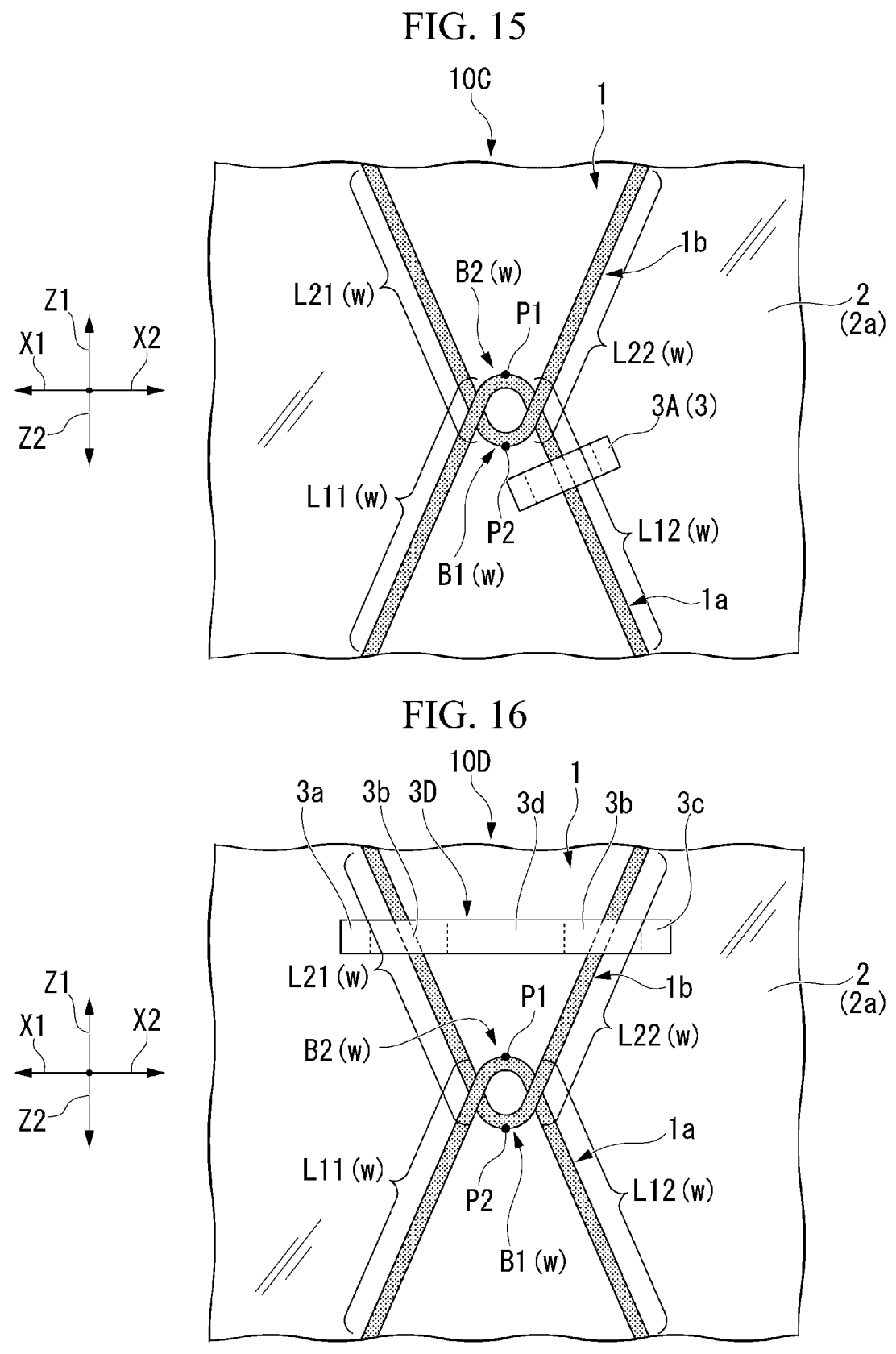

FIG. 15 is a schematic diagram showing an example of a cover stent according to a third modification of the first embodiment of the present invention.

The third modification is a particularly suitable example when one restricting member 3 is provided in the vicinity of the loop intersection LC.

As shown in FIG. 15, the cover stent 10C of this modification is configured by deleting the restricting member 3B in the second modification. Hereinafter, the points different from the second modification will be mainly described.

Since this modification is an example in which the restricting member 3B in the second modification is deleted, the movement of the second bending portion 1b in the axial direction is not blocked by the restricting member 3A as in the second modification. Therefore, the second bending portion 1b can move in the axial direction through the upper side of the restricting member 3A.

As for the first bending portion 1a, since the second bending portion 1b is not provided with a restricting member for blocking the movement in the axial direction, the first bending portion 1a can move in the axial direction within the allowable range of the space S1 (not shown) in the restricting member 3A.

According to this modification, even if the restricting member 3A is arranged in the vicinity of the loop intersection LC in the undeformed state, the relative movement amount of the first bending portion 1a and the second bending portion 1b is less limited in the axial direction. Therefore, the bending performance is further improved.

Fourth Modification

FIG. 16 is a schematic diagram showing an example of a cover stent according to a fourth modification of the first embodiment of the present invention.

As shown in FIG. 16, in the cover stent 10D of the fourth modification, in the first embodiment, the restricting member 3 through which the first straight line portion L11 and the second straight line portion L12 are inserted is deleted, and a restricting member 3D is provided in place of the two restricting members 3 through which the third straight line portion L21 and the fourth straight line portion L22 are inserted. Hereinafter, the points different from the first embodiment will be mainly described.

The restricting member 3D is a strip-shaped member longer than the restricting member 3. The length of the restricting member 3D is a length capable of crossing the third straight line portion L21 and the fourth straight line portion L22 of the second bending portion 1b in the X direction. The width of the restricting member 3D in the lateral direction may be the same as the width of the restricting member 3 in the lateral direction.

The restricting member 3D includes a joint portion 3a, a position restricting portion 3b, a joint portion 3d, a position restricting portion 3b, and a joint portion 3c in this order from the end portion in the X1 direction to the end portion in the X2 direction. The joint portions 3a and 3c and each position restricting portion 3b have the same configuration as that of the first embodiment.

In this modification, the joint portion 3a is joined to the outer cover 2 at a position closer to the X1 direction than the third straight portion L21. A third straight line portion L21 is inserted through the position restricting portion 3b connected to the joint portion 3a.

The joint portion 3c is joined to the outer cover 2 at a position closer to the X2 direction than the fourth straight line portion L22. A fourth straight line portion L22 is inserted through the position restricting portion 3b connected to the joint portion 3c.

Both ends of the joint portion 3d in the longitudinal direction are connected to the end portions of each position restricting portion 3b. The joint portion 3d is joined to the outer cover 2 between the position restricting portions 3b in the same manner as the joint portions 3a and 3c. However, the joint portion 3d does not have to be entirely joined to the outer cover 2, and may be connected to the outer cover 2 at least in the vicinity of the connection portion with each position restricting portion 3b.

The restricting member 3D is connected to the outer cover 2 by the joint portions 3a, 3d, and 3c in a posture in which it extends in the X direction.

The restricting member 3D is a single member and restricts the positions of both the third straight line portion L21 and the fourth straight line portion L22 in the second bending portion 1b.

The action related to the axial movement of the second bending portion 1b is the same as the case where the position is restricted by the two restricting members 3 through which the third straight portion L21 and the fourth straight portion L22 are respectively inserted.

According to this modification, by providing one restricting member 3D, the same operation as when the restricting member 3 is provided at two locations can be obtained, so that the number of parts of the cover stent 10D can be reduced and the manufacturing efficiency can be improved.

Although the example of using the restricting member 3D for the position restricting of the second bending portion 1b has been described above, the restricting member 3D may be used for the position restricting of the first bending portion 1a.

Fifth Modification

Figure 17:
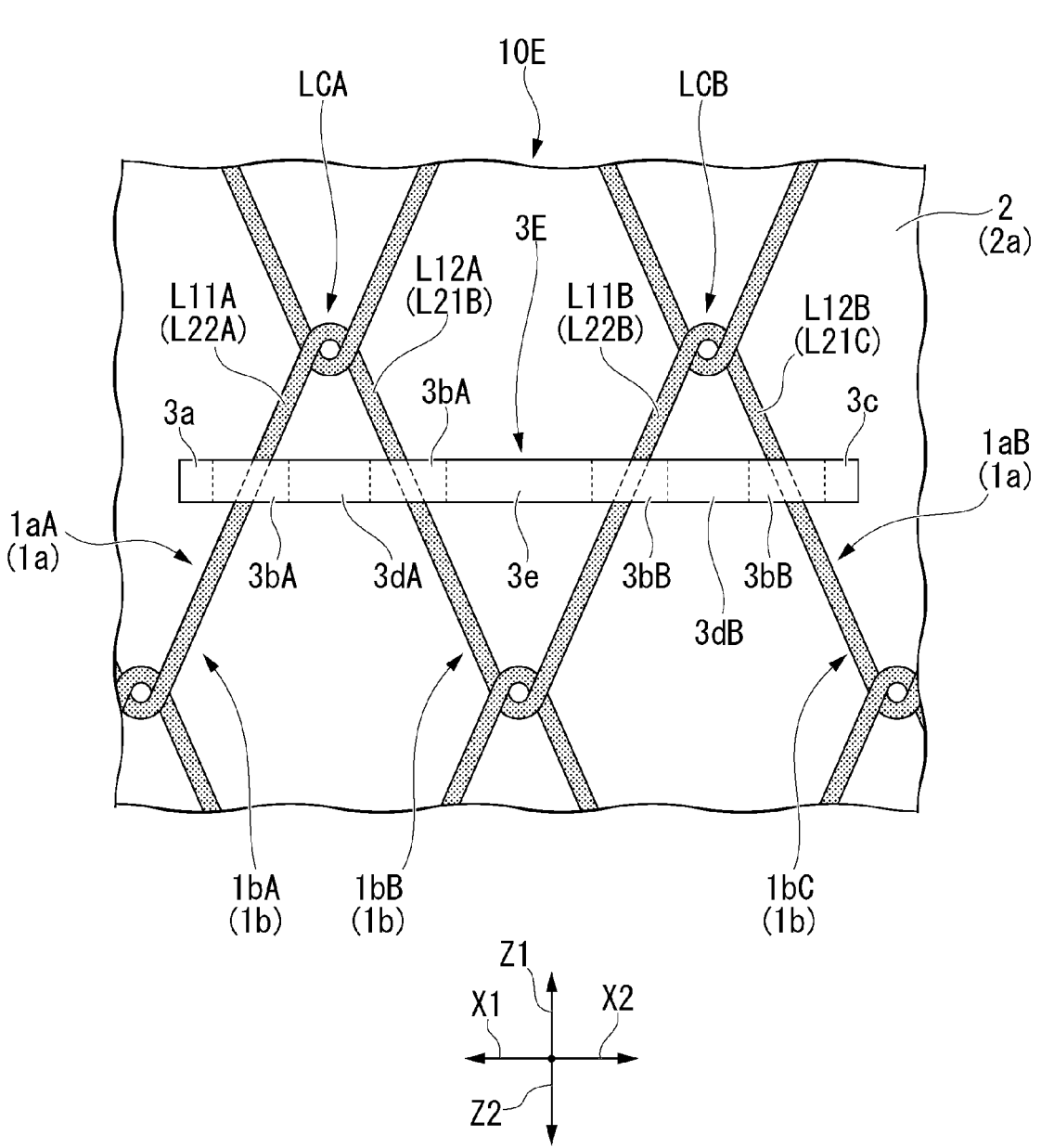
FIG. 17 is a schematic diagram showing an example of a cover stent according to a fifth modification of the first embodiment of the present invention.

FIG. 17 is a schematic diagram showing an example of a cover stent according to a fifth modification of the first embodiment of the present invention.

As shown in FIG. 17, the cover stent 10E of the fifth modification includes the restricting member 3E instead of the restricting member 3D of the fourth modification. Hereinafter, the points different from the fourth modification will be mainly described.

Each straight line portion in the first bending portion 1a adjacent to each other in the circumferential direction is inserted into the restricting member 3E. In the following, the first bending portions 1a adjacent to each other are referred to as first bending portions 1aA and 1aB (first bending portion group) in order in the X2 direction, and each portion related to each first bending portion 1a is also distinguished by adding subscripts A and B to the above-mentioned reference numerals.

The restricting member 3E is longer than the restricting member 3D, and is formed in the same manner as the restricting member 3D except that it provides the joint portion 3a, the position restricting portion 3bA, the joint portion 3dA, the position restricting portion 3bA, the joint portion 3e, the position restricting portion 3bB, the joint portion 3dB, the position restricting portion 3bB, and the joint portion 3c in this order from the end portion in the X1 direction to the end portion in the X2 direction. The joint portions 3*a* and 3*c* have the same configuration as that of the fourth modification. The joint portions 3*d*A and 3*d*B and the position restricting portions 3*b*A and 3*b*B have the same configurations as the joint portion 3*d* and the position restricting portion 3*b* in the fourth modification, respectively.

In this modification, the joint portion 3*a* is joined to the outer cover 2 at a position closer to the X1 direction than the first straight line portion L11A. A first straight line portion L11A is inserted through the position restricting portion 3*b*A connected to the joint portion 3*a*.

The joint portion 3*c* is joined to the outer cover 2 at a position closer to the X2 direction than the second straight portion L12B. A second straight line portion L12B is inserted through the position restricting portion 3*b*B connected to the joint portion 3*c*.

The joint portions 3*d*A and 3*d*B are configured in the same manner as the joint portion 3*d* in the fourth modification except for the joint position. The joint portion 3*d*A is joined to the outer cover 2 between the first straight line portion L11A and the second straight line portion L12A, and the joint portion 3*d*B is joined to the outer cover 2 between the first straight line portion L11B and the second straight line portion L12B.

Both ends of the joint portion 3*e* in the longitudinal direction are connected to the ends of the position restricting portions 3*b*A and 3*b*B. The joint portion 3*e* is joined to the outer cover 2 between the position restricting portions 3*b*A and 3*b*B in the same manner as the joint portion 3*d* in the fourth modification.

The restricting member 3E is connected to the outer cover 2 by the joint portions 3*a*, 3*d*A, 3*e*, 3*d*B, and 3*c* in a posture in which it extends in the X direction.

The restricting member 3E is a single member that restricts a position of a first straight line portion L11A and a second straight line portion L12A in the first bending portion 1*a*A and a first straight line portion L11B and a second straight line portion L12B in the first bending portion 1*a*B.

The action related to the axial movement of the first bending portions 1*a*A and 1*a*B is the same as the case where the positions of the first straight portions L11A and L11B and the second straight portions L12A and L12B are restricted by the two restricting members 3D into which the first straight portions L11A and L11B are inserted.

According to this modification, by providing one restricting member 3E, the same operation as when the restricting member 3D is provided at two locations can be obtained, so that the number of parts of the cover stent 10E can be reduced and the manufacturing efficiency can be improved.

In the above, the restricting member 3E of this modification has been described as a member that restricts the positions of the first bending portions 1*a*A and 1*a*B forming the loop intersection LCA and LCB. However, the first straight line portion L11A is also the fourth straight line portion L22A of the second bending portion 1*b*A on the lower side of the drawing. The second straight line portion L12A and the first straight line portion L11B are also the third straight line portion L21B and the fourth straight line portion L22B of the second bending portion 1*b*B adjacent to the second bending portion 1*b*A in the X2 direction. The second straight line portion L12B is also the third straight line portion L21C of the second bending portion 1*b*C adjacent to the second bending portion 1*b*B in the X2 direction.

Therefore, the restricting member 3E is also a member that restricts the positions of the four straight portions in the second bending portions 1*b*A, 1*b*B, and 1*b*C (second bending portion group).

Sixth Modification

Figure 18:
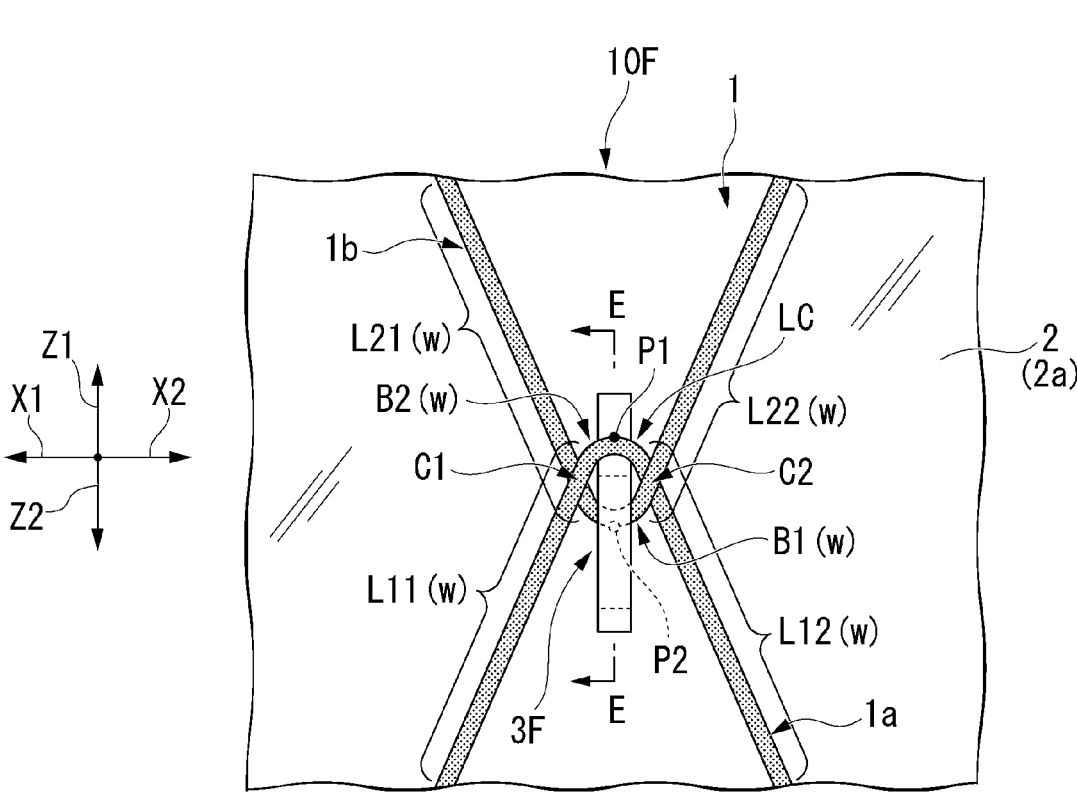
FIG. 18 is a schematic diagram showing an example of a cover stent according to a sixth modification of the first embodiment of the present invention.
Figure 19:
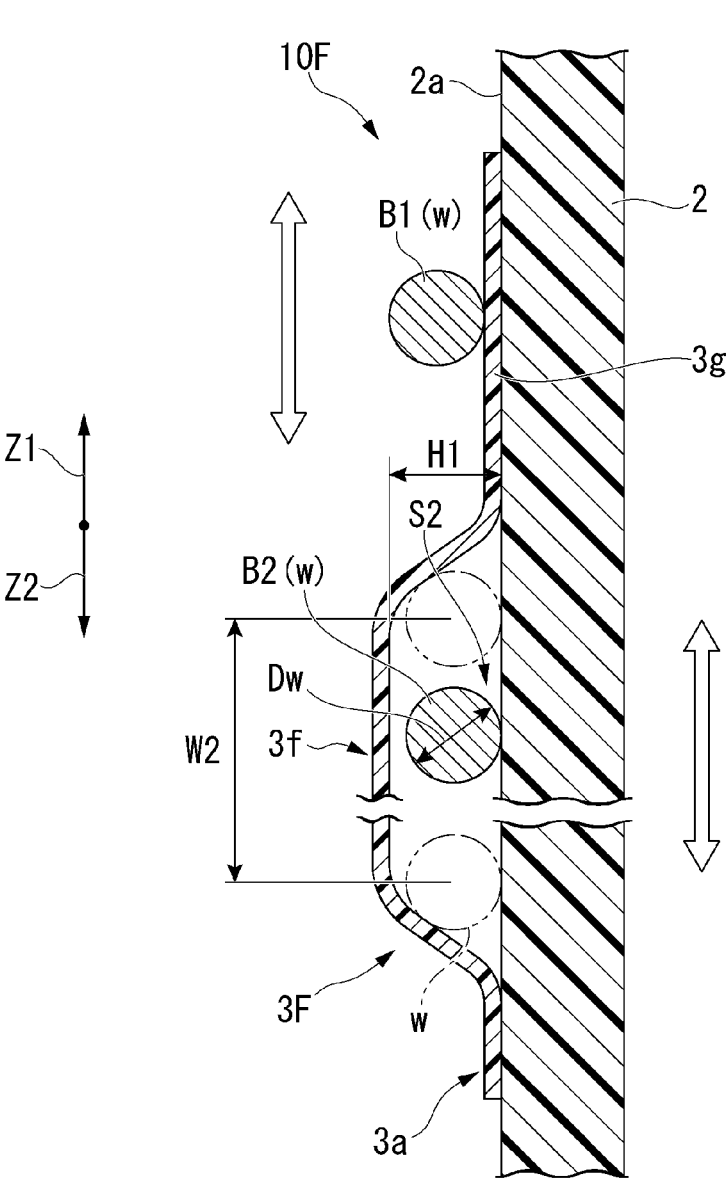
FIG. 19 is a cross-sectional view taken along the line E-E in FIG. 18.

FIG. 18 is a schematic diagram showing an example of a cover stent according to a sixth modification of the first embodiment of the present invention. FIG. 19 is a cross-sectional view taken along the line E-E in FIG. 18.

As shown in FIG. 18, the cover stent 10F of the sixth modification includes the restricting member 3F instead of the restricting member 3 in the first embodiment. Hereinafter, the points different from the first embodiment will be mainly described.

The restricting member 3F is a member that restricts the position of the inserted first bending portion 1*a*, or second bending portion 1*b* by inserting the first bending portion 1*a* or the second bending portion 1*b* in the loop intersection LC.

In the following, an example of a case where the second bending portion 1*b* is inserted through the restricting member 3F will be described with reference to FIG. 18.

The restricting member 3F is arranged in a positional relationship that intersects the bending portion B2 of the second bending portion 1*b* in the radial direction in the Z direction. The restricting member 3F includes a joint portion 3*a*, a position restricting portion 3*f*, and a joint portion 3*g* from the end portion in the Z2 direction to the end portion in the Z1 direction. The joint portion 3*a* has the same configuration as that of the first embodiment.

As shown in FIG. 19, the position restricting portion 3*f* is configured in the same manner as the position restricting portion 3*b* except that the space S2 is formed instead of the space S1.

The space S2 is the same as the space S1 except that the distance that the wire w can move in the Z direction is W2. However, the width in the circumferential direction in the space S2 is not particularly limited as long as it can be arranged in the loop intersection LC in the undeformed state.

The size of W2 may be set according to the movable amount required for the second bending portion 1*b*. However, it is more preferable that the length of W2 be shorter than half of the length of one step so as not to hinder the movement of the first bending portion 1*a* facing the bending portion B2 on the lower side of the drawing.

The space S2 has a first size H1 similar to the space S1 in the radial direction.

For example, the joint portion 3*g* may be configured in the same manner as the joint portion 3*c*.

For example, as shown in FIG. 19, the joint portion 3*g* may have an axial length that overlaps with the movable range in the axial direction of the bending portion B1 when viewed from the radial direction. In this case, the bending portion B1 slides and moves on the joint portion 3*g* extending linearly in the Z direction. Therefore, the contact area with the inner peripheral surface 2*a* at the time of movement can be reduced as compared with the case where the joint portion 3*g* does not overlap with the movement range of the bending portion B1. As a result, the relative movement between the first bending portion 1*a* and the outer cover 2 becomes smoother. In particular, if a material having a low coefficient of friction with the wire w is used as the material of the joint portion 3*g*, the frictional force acting on the first bending portion 1*a* during relative movement is reduced.

The joint portions 3*d*A and 3*d*B are configured in the same manner as the joint portion 3*d* in the fourth modification except for the joint position. The joint portion 3dA is joined to the outer cover 2 between the first straight line portion L11A and the second straight line portion L12A, and the joint portion 3dB is joined to the outer cover 2 between the first straight line portion L11B and the second straight line portion L12B.

According to this modification, the movable amount of the second bending portion 1b with respect to the outer cover 2 in the axial direction is restricted by the restricting member 3F. As a result, the second bending portion 1b can move in the axial direction along the inner peripheral surface 2a within the range of W2.

The first bending portion 1a is movable along the inner peripheral surface 2a on the Z1 direction side of the end portion of the position restricting portion 3f in the Z1 direction. This enables the relative movement of the first bending portion 1a and the second bending portion 1b.

Seventh Modification

Figure 20:
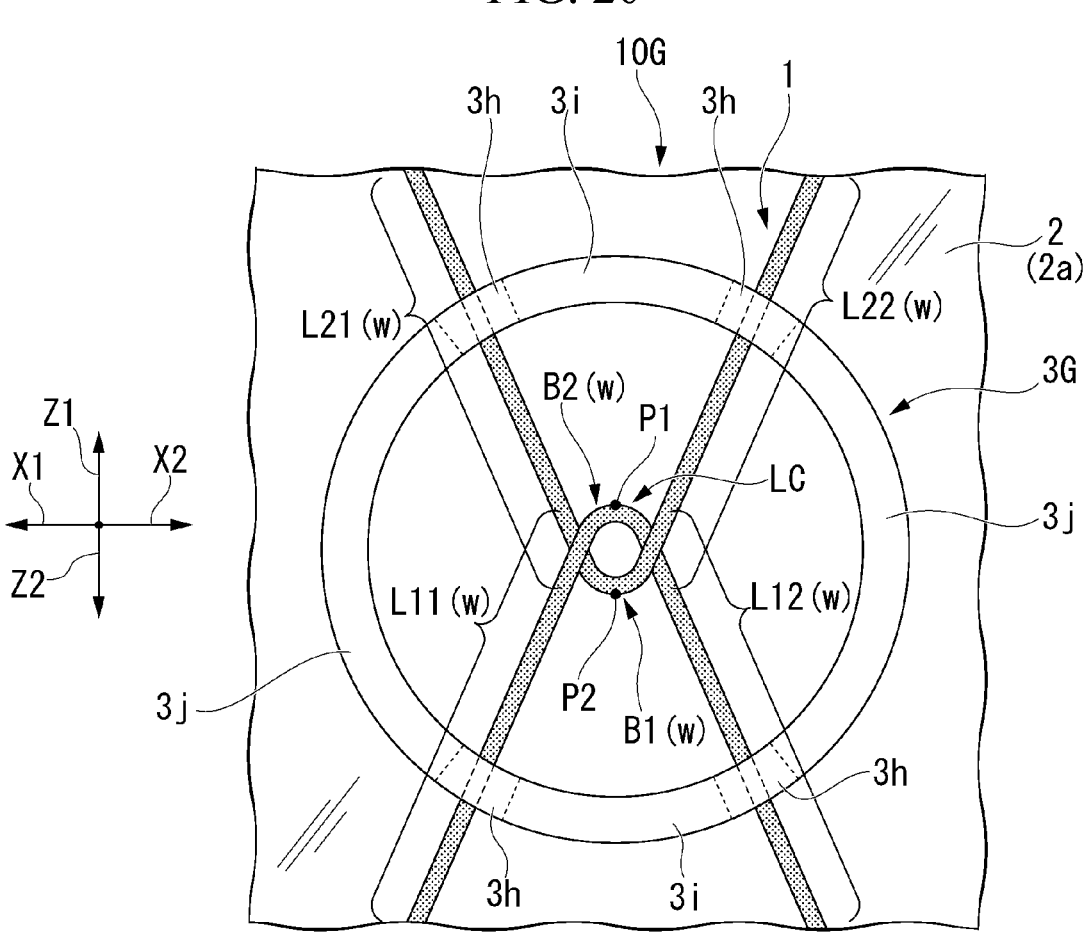
FIG. 20 is a schematic diagram showing an example of a cover stent according to a seventh modification of the first embodiment of the present invention.

FIG. 20 is a schematic diagram showing an example of a cover stent according to a seventh modification of the first embodiment of the present invention.

As shown in FIG. 20, the cover stent 10G of the seventh modification includes the restricting member 3G instead of the restricting member 3 in the first embodiment. Hereinafter, the points different from the first embodiment will be mainly described.

The restricting member 3G is formed in a loop shape surrounding the loop intersection LC when viewed from the radial direction. The loop shape of the restricting member 3G may be a closed loop or an open loop.

For example, an example of a closed loop is an annular loop or a substantially annular loop. Other examples of closed loops include rectangular loops, polygonal loops, and the like.

For example, as an example of the closed loop, there is a substantially C-shaped loop in which an opening is formed in a part of the various closed loop shapes described above.

In the following, as an example, the radial shape of the restricting member 3G will be described as an annular closed loop shown in FIG. 20.

The restricting member 3G includes two joint portions 3i and two joint portions 3j that connect in the circumferential direction the four position restricting portions 3h into which the first straight line portion L11, the second straight line portion L12, the third straight line portion L21, and the fourth straight line portion L22 are inserted, and the position regulating portions 3h adjacent to each other in the circumferential direction.

Since each position restricting portion 3h forms a part of the annular shape, it is configured in the same manner as the position restricting portion 3b in the first embodiment except that it is curved in an arc shape in the longitudinal direction.

Each joint portion 3i is formed in an arc shape connecting between each position restricting portion 3h through which the first straight line portion L11 and the second straight line portion L12 are inserted, and between each position restricting portion 3h through which the third straight portion L21 and the fourth straight portion L22 are inserted. Each joint portion 3i is joined to the outer cover 2 in the same manner as the joint portion 3d in the fourth modification, at least in the vicinity of each position restricting portion 3h.

Each joint portion 3j is formed in an arc shape connecting between each position restricting portion 3h through which the first straight line portion L11 and the third straight line portion L21 are inserted, and between each position restricting portion 3h through which the second straight line portion L12 and the fourth straight line portion L22 are inserted. Each joint portion 3j is joined to the outer cover 2 in the same manner as each joint portion 3i.

According to this modification, by providing one restricting member 3G, the same operation as when the restricting member 3 is provided at four locations can be obtained as in the first embodiment, so that the number of parts of the cover stent 10G can be reduced and the manufacturing efficiency can be improved.

According to this modification, since the restricting member 3G may be arranged around the loop intersection LC, positioning when joining the restricting member 3G to the outer cover 2 becomes easy.

Eighth Modification

Figure 21:
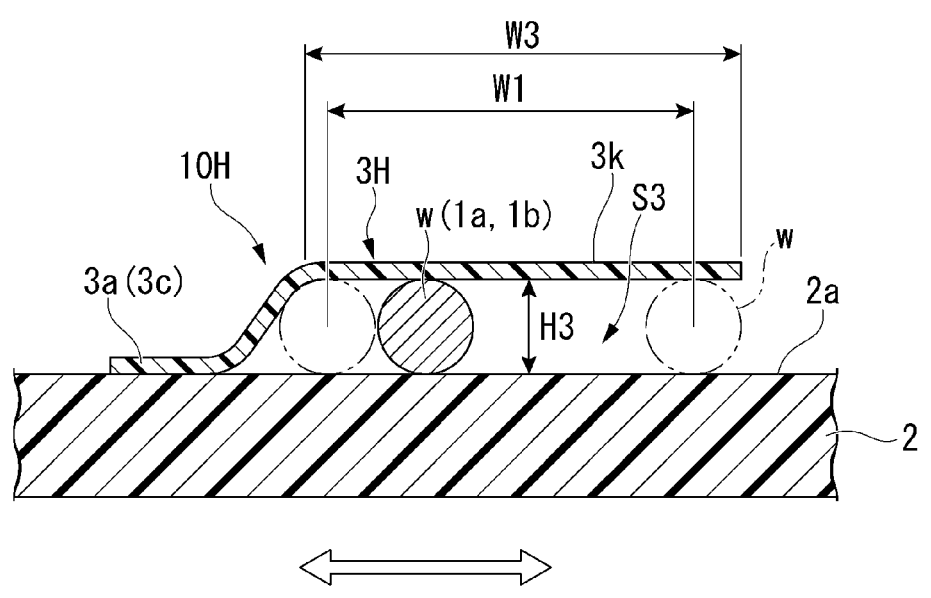
FIG. 21 is a schematic diagram showing an example of a cover stent according to an eighth modification of the first embodiment of the present invention.

FIG. 21 is a schematic diagram showing an example of a cover stent according to an eighth modification of the first embodiment of the present invention.

As shown in FIG. 21, the cover stent 10H of the eighth modification includes the restricting member 3H instead of the restricting member 3 in the first embodiment. Hereinafter, the points different from the first embodiment will be mainly described.

The restricting member 3H has a different cross-sectional shape from the restricting member 3. The restricting member 3H includes a joint portion 3a or a joint portion 3c similar to that of the first embodiment, and a position restricting portion 3k.

The position restricting portion 3k is connected to the joint portion 3a (3c) and is formed so as to be separated from the inner peripheral surface 2a. In the example shown in FIG. 21, the position restricting portion 3k extends obliquely inward in the radial direction from the end portion of the joint portion 3a (3c), and then has a substantially constant height from the inner peripheral surface 2a.

A space S3 is formed between the position restricting portion 3k and the inner peripheral surface 2a so that the wire w can be inserted and the inserted wire w can move at least along the longitudinal direction of the mesh tube 1.

In the space S3, the size between the flat portion of the position restricting portion 3k and the inner peripheral surface 2a is H3 (first size) having a diameter Dw or less of the wire w. Therefore, the position restricting portion 3k is in contact with the wire w inserted into the space S3. It is more preferable that the position restricting portion 3k urge the wire w so as not to separate from the inner peripheral surface 2a when the wire w moves.

In the space S3, the size of the restricting member 3 in the longitudinal direction can be appropriately set according to the required movement amount of the wire w. For example, the length V (second size) of the flat portion of the position restricting portion 3k may be a length such that the movable length of the wire w in the longitudinal direction is W1 or more.

According to this modification, since the restricting member 3H is joined to the outer cover 2 at one joint portion 3a (3c), it is joined at two places as in the restricting member 3 of the first embodiment. The cover stent 10H can be manufactured more quickly than the above.

Ninth Modification

Figures 22, 23:
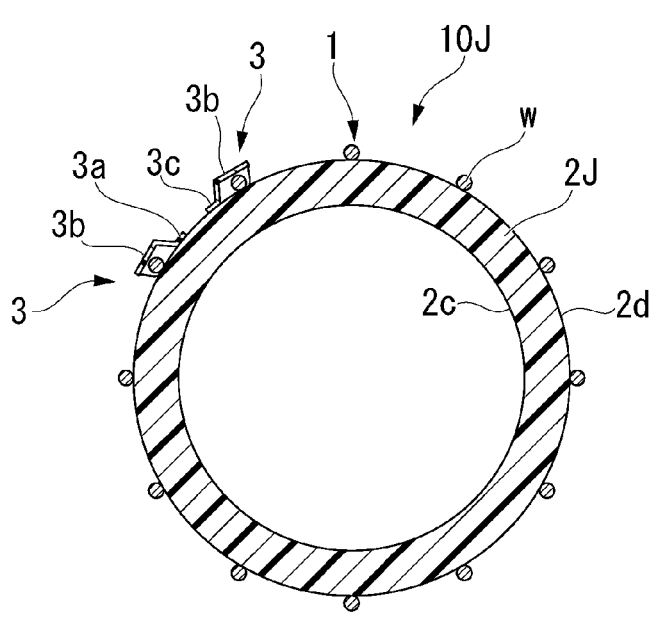
FIG. 22 is a schematic diagram showing an example of a cover stent according to a ninth modification of the first embodiment of the present invention.
FIG. 23 is a cross-sectional view showing an example of a cover stent according to a second embodiment of the present invention.

FIG. 22 is a schematic diagram showing an example of a cover stent according to a ninth modification of the first embodiment of the present invention.

As shown in FIG. 22, the cover stent 10I of the ninth modification includes the restricting member 3I instead of the restricting member 3 in the first embodiment. Hereinafter, the points different from the first embodiment will be mainly described.

The restricting member 3I has a different cross-sectional shape from the restricting member 3. The restricting member 3I includes two protrusions 3m and a plate-shaped portion 3n.

Each protrusion 3m has an appropriate shape protruding from the inner peripheral surface 2a. For example, the shape of each protrusion 3m may be columnar, conical, dome-shaped, or the like.

The height (first size) of each protrusion 3m from the inner peripheral surface 2a is the above-mentioned H1. The distance W4 (second size) between the protrusions 3m is a distance at which the movable distance of the wire w between the protrusions 3m is equal to or greater than the above-mentioned W1.

Each protrusion 3m may be provided as a separate member from the outer cover 2 and the plate-shaped portion 3n described later, or may be provided with the same material as at least one of the outer cover 2 and the plate-shaped portion 3n.

The plate-shaped portion 3n is joined to the upper end portion of each protrusion 3m. The shape of the plate-shaped portion 3n seen from the radial direction is a rectangular shape similar to that of the position restricting portion 3b.

The method of joining the plate-shaped portion 3n and each protrusion 3m is not particularly limited. For example, the plate-shaped portion 3n and each protrusion 3m may be formed by fusion, adhesion, or the like.

With such a configuration, a space S4 surrounded by an inner peripheral surface 2a, each protrusion 3m, and a plate-shaped portion 3n is formed inside the restricting member 3I. Similar to the space S1 in the first embodiment, the space S4 has a first size substantially equal to Dw and a second size larger than the first size in the circumferential direction of the outer cover 2.

The restricting member 3I of this modification is an example in which the space S4 corresponding to the space S1 can be formed by a configuration different from that of the restricting member 3.

According to the cover stent 10I of this modification, the wires w of the first bending portion 1a and the second bending portion 1b can be moved in the space S3 as in the first embodiment. Therefore, the bending performance and the shape maintaining performance can be improved in the same manner as in the cover stent 10 of the first embodiment.

Second Embodiment

The cover stent of the second embodiment of the present invention will be described.

FIG. 23 is a cross-sectional view showing an example of a cover stent according to a second embodiment of the present invention.

As shown in FIG. 23, the cover stent 10J of the present embodiment includes an inner cover 2J (cover) instead of the outer cover 2 of the cover stent 10 of the first embodiment. Hereinafter, the points different from the first embodiment will be mainly described.

The inner cover 2J is a circular tube having an inner peripheral surface 2c on the inner side and an outer peripheral surface 2d (the surface of the cover) on the outer side and covering the inside of the mesh tube 1. The diameter of the outer peripheral surface 2d is not particularly limited as long as the inner peripheral portion of the mesh tube 1 can be in contact with the entire circumference. It is more preferable that the diameter of the outer peripheral surface 2d be substantially equal to the inner diameter of the mesh tube 1 in the undeformed state.

The inner cover 2J has the same configuration as the outer cover 2 except for the diameters of the inner peripheral surface 2c and the outer peripheral surface 2d.

In the present embodiment, the mesh tube 1 is connected to the inner cover 2J on the outer peripheral surface 2d by the same restricting member 3 as in the first embodiment with the inner cover 2J passed inside. However, the restricting member 3 in the present embodiment is provided so as to straddle the wire w forming the first bending portion or the second bending portion on the outer peripheral surface 2d from the outside in the radial direction.

According to the cover stent 10J of the present embodiment, it is configured in the same manner as the cover stent 10 of the first embodiment except that the mesh tube 1 is arranged outside the inner cover 2J. Therefore, as in the first embodiment, the bending performance and the shape maintaining performance can be improved.

In each embodiment and each modification, the shape of the restricting member is described as a strip-shaped example. However, the restricting member is not limited to a strip shape as long as a space can be formed between the surface of the cover and the surface of the cover so that the wire at at least one of the first bending portion and the second bending portion can be movably inserted along the surface of the cover. For example, the restricting member may be rod-shaped, stranded wire-shaped, or the like.

In the first embodiment, an example in which the restricting member 3 is orthogonal to the wire w when viewed from the radial direction has been described. However, if the required amount of movement is obtained for the first bending portion 1a and the second bending portion 1b, the inclination angle between the restricting member 3 and the wire w is not limited to 90°. For example, the restricting member 3 may be arranged so as to extend in the circumferential direction, or may be arranged so as to extend in the axial direction.

In the first modification, the example in which the joining member 4 is provided at a portion away from the intersection position of the simple intersection SC has been described. However, the joining member may be provided at the intersection position of the simple intersection SC as long as the wire can be fixed. For example, the joining member may be formed of an adhesive-cured product that is in contact with the surface of the cover at the intersection position of the simple intersection SC and each wire at the intersection position.

In each embodiment and each modification, the example in which the restricting member is connected to the cover by being joined to the cover has been described. However, the restricting member may be connected to the cover by being sewn to the cover in a state of being prevented from coming off.

Further, the restricting member may be thread-shaped or strip-shaped, sewn to the cover, and formed by a seam forming a loop above the cover.

In the explanation of the fifth modification, the example in which the restricting member 3E is arranged so as to straddle two first bending portions 1a or three second bending portions 1b adjacent to each other in the circumferential direction has been described. However, the restricting member may be arranged so as to straddle four or more first bending portions or second bending portions depending on the length. For example, the restricting member may be provided so as to orbit the mesh tube 1 one or more times in the circumferential direction. For example, when the restricting member orbits one or more times, it may orbit in a spiral shape.

In each embodiment and each modification, when the restricting member is provided, at most one restricting member is provided in each of the first to fourth straight lines. However, a plurality of restricting members may be provided in at least one straight line portion of the first to fourth straight line portions.

Although the preferred embodiments and modifications of the present invention have been described above, the present invention is not limited to these embodiments and modifications. It is possible to add, omit, replace, and make other changes to the configuration without departing from the spirit of the present invention.

Further, the present invention is not limited by the above description, but only by the claims of the attachment.

According to each of the above embodiments and modifications, it is possible to provide a cover stent capable of improving bending performance and shape maintenance performance.

What is claimed is:

1. A cover stent comprising:

a mesh tube knitted into a tube shape by a wire, the wire including a first bending portion protruding toward a first end portion in a longitudinal direction of the tube shape and a second bending portion protruding toward a second end portion opposite to the first end portion in the longitudinal direction, the first bending portion and the second bending portion intersecting each other at an intersection of the first bending portion and the second bending portion by being twisted once;

a cover that covers outside or inside of the mesh tube; and at least one restricting member connected to the cover with a space, the wire in at least one of the first bending portion and the second bending portion being movably inserted into the space along a surface of the cover, wherein, the first bending portion is closer to the cover than the second bending portion at the intersection; and the restricting member is disposed in a vicinity of the intersection where the first bending portion and the second bending portion intersect with each other, and the restricting member is only disposed on the first bending portion located closer to the cover among the first and second bending portions located at the intersection.

* * * * *